(12) United States Patent
Chen et al.

(10) Patent No.: US 11,759,632 B2
(45) Date of Patent: Sep. 19, 2023

(54) FIXATION COMPONENTS FOR IMPLANTABLE MEDICAL DEVICES

(71) Applicant: Medtronic, Inc., Minneapolis, MN (US)

(72) Inventors: Xin Chen, Blaine, MN (US); Vladimir Grubac, Brooklyn Park, MN (US); Brian P. Colin, Anoka, MN (US); Kathryn Hilpisch, Cottage Grove, MN (US); Michael D. Eggen, Chisago City, MN (US)

(73) Assignee: Medtronic, Inc., Minneapolis, MN (US)

( * ) Notice: Subject to any disclaimer, the term of this patent is extended or adjusted under 35 U.S.C. 154(b) by 294 days.

(21) Appl. No.: 16/825,143

(22) Filed: Mar. 20, 2020

(65) Prior Publication Data

US 2020/0306522 A1    Oct. 1, 2020

Related U.S. Application Data

(60) Provisional application No. 62/825,233, filed on Mar. 28, 2019.

(51) Int. Cl.
*B21D 39/02* (2006.01)
*A61N 1/05* (2006.01)

(52) U.S. Cl.
CPC ............. *A61N 1/059* (2013.01); *B21D 39/02* (2013.01)

(58) Field of Classification Search
CPC ............... A61N 1/059; A61N 1/37205; A61N 1/37518; A61N 1/3756; A61N 1/0573; B21D 39/02
See application file for complete search history.

(56) References Cited

U.S. PATENT DOCUMENTS

| | | |
|---|---|---|
| 3,717,151 A | 2/1973 | Collett |
| 3,754,555 A | 8/1973 | Schmitt |
| 3,814,104 A | 6/1974 | Imich |

(Continued)

FOREIGN PATENT DOCUMENTS

| | | |
|---|---|---|
| CA | 1003 904 A1 | 1/1977 |
| CA | 2477207 A1 | 2/2006 |

(Continued)

OTHER PUBLICATIONS

Notice of Allowance from U.S. Appl. No. 16/158,724, dated Mar. 19, 2021, 7 pp.

(Continued)

*Primary Examiner* — Ankit D Tejani
*Assistant Examiner* — Joshua Brendon Solomon
(74) *Attorney, Agent, or Firm* — Shumaker & Sieffert, P.A.

(57) ABSTRACT

An example fixation component for an implantable medical device (IMD) includes a base and a plurality of tines configured be deployed with a target deployment stiffness to engage tissue a target implant site while maintaining a target deflection stiffness after deployment. The base defines a longitudinal axis of the fixation component and is fixedly attached near the distal end of the IMD. Each tine is spaced apart from one another around a perimeter of the distal end of the IMD and extend from the base. A shape of each tine is selected to control each of the target deployment stiffness and target deflection stiffness.

31 Claims, 16 Drawing Sheets

(56) References Cited

U.S. PATENT DOCUMENTS

| | | |
|---|---|---|
| 3,835,864 A | 9/1974 | Rasor et al. |
| 3,902,501 A | 9/1975 | Citron et al. |
| 3,943,936 A | 3/1976 | Rasor |
| 3,971,364 A | 7/1976 | Fletcher et al. |
| 3,976,082 A | 8/1976 | Schmitt |
| 4,103,690 A | 8/1978 | Harris |
| 4,112,952 A | 9/1978 | Thomas et al. |
| 4,142,530 A | 3/1979 | Wittkampf |
| 4,269,198 A | 5/1981 | Stokes |
| 4,280,512 A | 7/1981 | Karr |
| 4,301,815 A | 11/1981 | Doring |
| 4,402,328 A | 9/1983 | Doring |
| 4,409,994 A | 10/1983 | Doring |
| 4,502,492 A | 3/1985 | Bornzin |
| 4,662,382 A | 5/1987 | Sluetz et al. |
| 4,898,577 A | 2/1990 | Badger et al. |
| 4,913,164 A | 4/1990 | Greene et al. |
| 4,936,823 A | 6/1990 | Colvin |
| 5,003,990 A | 4/1991 | Osypka |
| 5,057,114 A | 10/1991 | Wittich et al. |
| 5,129,749 A | 7/1992 | Sato |
| 5,171,233 A | 12/1992 | Amplatz et al. |
| 5,193,540 A | 3/1993 | Schulman et al. |
| 5,257,634 A | 11/1993 | Kroll |
| 5,282,845 A | 2/1994 | Bush et al. |
| 5,300,107 A | 4/1994 | Stokes et al. |
| 5,318,528 A | 6/1994 | Heaven et al. |
| 5,336,253 A | 8/1994 | Gordon et al. |
| 5,405,367 A | 4/1995 | Schulman et al. |
| 5,405,374 A | 4/1995 | Stein |
| 5,411,535 A | 5/1995 | Fujii et al. |
| 5,425,756 A | 6/1995 | Heil et al. |
| 5,443,492 A | 8/1995 | Stokes et al. |
| 5,492,119 A | 2/1996 | Abrams |
| 5,522,875 A | 6/1996 | Gates et al. |
| 5,522,876 A | 6/1996 | Rusink |
| 5,545,201 A | 8/1996 | Helland et al. |
| 5,545,206 A | 8/1996 | Carson |
| 5,562,723 A | 10/1996 | Rugland et al. |
| 5,573,540 A | 11/1996 | Yoon |
| 5,575,814 A | 11/1996 | Giele et al. |
| 5,578,068 A | 11/1996 | Laske et al. |
| 5,683,447 A | 11/1997 | Bush et al. |
| 5,697,936 A | 12/1997 | Shipko et al. |
| 5,716,390 A | 2/1998 | Li |
| 5,716,391 A | 2/1998 | Grandjean |
| 5,755,764 A | 5/1998 | Schroeppel |
| 5,776,178 A | 7/1998 | Pohndorf et al. |
| 5,807,399 A | 9/1998 | Laske et al. |
| 5,837,006 A | 11/1998 | Ocel et al. |
| 5,837,007 A | 11/1998 | Altman et al. |
| 5,851,226 A | 12/1998 | Skubitz et al. |
| 5,871,531 A | 2/1999 | Struble |
| 5,908,381 A | 6/1999 | Aznoian et al. |
| 5,908,447 A | 6/1999 | Schroeppel et al. |
| 6,007,558 A | 12/1999 | Ravenscroft et al. |
| 6,041,258 A | 3/2000 | Cigaina et al. |
| 6,055,457 A | 4/2000 | Bonner |
| 6,074,401 A | 6/2000 | Gardnier et al. |
| 6,078,840 A | 6/2000 | Stokes |
| 6,093,177 A | 7/2000 | Javier et al. |
| 6,129,749 A | 10/2000 | Bartig et al. |
| 6,132,456 A | 10/2000 | Sommer et al. |
| 6,151,525 A | 11/2000 | Soykan et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,251,104 B1 | 6/2001 | Kesten et al. |
| 6,286,512 B1 | 9/2001 | Loeb et al. |
| 6,290,719 B1 | 9/2001 | Garberoglio |
| 6,321,124 B1 | 11/2001 | Cigaina |
| 6,322,548 B1 | 11/2001 | Payne et al. |
| RE37,463 E | 12/2001 | Altman |
| 6,358,256 B1 | 3/2002 | Reinhardt |
| 6,363,938 B2 | 4/2002 | Saadat et al. |
| 6,381,495 B1 | 4/2002 | Jenkins |
| 6,381,500 B1 | 4/2002 | Fischer, Sr. |
| 6,408,214 B1 | 6/2002 | Williams et al. |
| 6,409,674 B1 | 6/2002 | Brockway et al. |
| 6,458,145 B1 | 10/2002 | Ravenscroft et al. |
| 6,477,423 B1 | 11/2002 | Jenkins |
| 6,500,182 B2 | 12/2002 | Foster |
| 6,510,332 B1 | 1/2003 | Greenstein |
| 6,510,345 B1 | 1/2003 | Van Bentem |
| 6,522,915 B1 | 2/2003 | Ceballos et al. |
| 6,572,587 B2 | 6/2003 | Lerman et al. |
| 6,575,967 B1 | 6/2003 | Leveen et al. |
| 6,582,441 B1 | 6/2003 | He et al. |
| 6,592,581 B2 | 7/2003 | Bowe |
| 6,623,518 B2 | 9/2003 | Thompson et al. |
| 6,626,915 B2 | 9/2003 | Leveillee |
| 6,638,268 B2 | 10/2003 | Niazi |
| 6,684,109 B1 | 1/2004 | Osypka |
| 6,711,443 B2 | 3/2004 | Osypka |
| 6,738,672 B2 | 5/2004 | Schulman |
| 6,743,240 B2 | 6/2004 | Smith et al. |
| 6,755,812 B2 | 6/2004 | Peterson et al. |
| 6,783,499 B2 | 8/2004 | Schwartz |
| 6,823,217 B2 | 11/2004 | Rutten |
| 6,909,920 B2 | 6/2005 | Lokhoff et al. |
| 6,915,149 B2 | 7/2005 | Ben-Haim |
| 6,944,507 B2 | 9/2005 | Froberg |
| 6,953,454 B2 | 10/2005 | Peterson et al. |
| 6,978,178 B2 | 12/2005 | Sommer et al. |
| 7,027,876 B2 | 4/2006 | Casavant et al. |
| 7,082,335 B2 | 7/2006 | Klein et al. |
| 7,082,336 B2 | 7/2006 | Ransbury |
| 7,085,606 B2 | 8/2006 | Flach et al. |
| 7,092,765 B2 | 8/2006 | Geske et al. |
| 7,092,766 B1 | 8/2006 | Salys et al. |
| 7,120,504 B2 | 10/2006 | Osypka |
| 7,130,700 B2 | 10/2006 | Gardeski |
| 7,149,587 B2 | 12/2006 | Wardle et al. |
| 7,158,838 B2 | 1/2007 | Seifert et al. |
| 7,162,310 B2 | 1/2007 | Doan |
| 7,181,288 B1 | 2/2007 | Rezai et al. |
| 7,187,982 B2 | 3/2007 | Seifert et al. |
| 7,200,437 B1 | 4/2007 | Nabutovsky et al. |
| 7,212,869 B2 | 5/2007 | Wahlstrom et al. |
| 7,229,415 B2 | 6/2007 | Schwartz |
| 7,251,532 B2 | 7/2007 | Hess et al. |
| 7,289,853 B1 | 10/2007 | Campbell et al. |
| 7,290,743 B2 | 11/2007 | Nowack |
| 7,313,445 B2 | 12/2007 | McVenes et al. |
| 7,326,231 B2 | 2/2008 | Phillips et al. |
| 7,328,071 B1 | 2/2008 | Stehr et al. |
| 7,331,922 B2 | 2/2008 | Mohl |
| 7,383,091 B1 | 6/2008 | Chitre et al. |
| 7,418,298 B2 | 8/2008 | Shiroff et al. |
| 7,450,999 B1 | 11/2008 | Karicherla et al. |
| 7,462,184 B2 | 12/2008 | Worley et al. |
| 7,463,933 B2 | 12/2008 | Wahlstrom et al. |
| 7,499,758 B2 | 3/2009 | Cates et al. |
| 7,509,169 B2 | 3/2009 | Eigler et al. |
| 7,515,971 B1 | 4/2009 | Doan |
| 7,532,939 B2 | 5/2009 | Sommer et al. |
| 7,558,631 B2 | 7/2009 | Cowan et al. |
| 7,634,319 B2 | 12/2009 | Schneider et al. |
| 7,647,109 B2 | 1/2010 | Hastings |
| 7,657,325 B2 | 2/2010 | Williams |
| 7,678,128 B2 | 3/2010 | Boyle et al. |
| 7,717,899 B2 | 5/2010 | Bowe et al. |
| 7,731,655 B2 | 6/2010 | Smith et al. |
| 7,734,343 B2 | 6/2010 | Ransbury et al. |
| 7,740,640 B2 | 6/2010 | Ginn |
| 7,785,264 B2 | 8/2010 | Hettrick et al. |
| 7,799,037 B1 | 9/2010 | He et al. |
| 7,801,624 B1 | 9/2010 | Flannery et al. |
| 7,835,801 B1 | 11/2010 | Sundararajan et al. |
| 7,840,281 B2 | 11/2010 | Kveen et al. |
| 7,840,283 B1 | 11/2010 | Bush et al. |
| 7,860,580 B2 | 12/2010 | Falk et al. |
| 7,875,049 B2 | 1/2011 | Eversull et al. |
| 7,890,186 B2 | 2/2011 | Wardle et al. |

(56) References Cited

U.S. PATENT DOCUMENTS

| | | |
|---|---|---|
| 7,904,179 B2 | 3/2011 | Rutten et al. |
| 7,920,928 B1 | 4/2011 | Yang et al. |
| 7,949,395 B2 | 5/2011 | Kuzma |
| 7,993,351 B2 | 8/2011 | Worley et al. |
| 8,010,209 B2 | 8/2011 | Jacobson |
| 8,012,127 B2 | 9/2011 | Lieberman |
| 8,032,219 B2 | 10/2011 | Neumann |
| 8,036,757 B2 | 10/2011 | Worley |
| 8,057,486 B2 | 11/2011 | Hansen |
| 8,082,035 B2 | 12/2011 | Glukhovsky |
| 8,103,361 B2 | 1/2012 | Moser |
| 8,108,054 B2 | 1/2012 | Helland |
| 8,142,347 B2 | 3/2012 | Griego et al. |
| 8,160,722 B2 | 4/2012 | Rutten et al. |
| 8,170,690 B2 | 5/2012 | Morgan et al. |
| 8,185,213 B2 | 5/2012 | Kveen et al. |
| 8,219,213 B2 | 7/2012 | Sommer et al. |
| 8,233,994 B2 | 7/2012 | Sommer et al. |
| 8,252,019 B2 | 8/2012 | Fleming, III |
| 8,262,672 B2 | 9/2012 | Neidert |
| 8,295,939 B2 | 10/2012 | Jacobson |
| 8,313,445 B2 | 11/2012 | Mishima et al. |
| 8,352,025 B2 | 1/2013 | Jacobson |
| 8,352,028 B2 | 1/2013 | Wenger |
| 8,353,940 B2 | 1/2013 | Benderev |
| 8,364,277 B2 | 1/2013 | Glukhovsky |
| 8,364,280 B2 | 1/2013 | Marnfeldt et al. |
| 8,406,900 B2 | 3/2013 | Barlov et al. |
| 8,406,901 B2 | 3/2013 | Starkebaum et al. |
| 8,418,362 B2 | 4/2013 | Zerfas et al. |
| 8,428,750 B2 | 4/2013 | Kolberg |
| 8,452,420 B2 | 5/2013 | Flach et al. |
| 8,478,431 B2 | 7/2013 | Griswold |
| 8,489,189 B2 | 7/2013 | Tronnes |
| 8,494,650 B2 | 7/2013 | Glukhovsky et al. |
| 8,504,156 B2 | 8/2013 | Bonner et al. |
| 8,518,060 B2 | 8/2013 | Jelich et al. |
| 8,527,068 B2 | 9/2013 | Ostroff |
| 8,532,790 B2 | 9/2013 | Griswold |
| 8,548,605 B2 | 10/2013 | Ollivier |
| 8,565,897 B2 | 10/2013 | Regnier et al. |
| 8,615,310 B2 | 12/2013 | Khairkhahan |
| 8,634,912 B2 | 1/2014 | Bornzin |
| 8,670,842 B1 | 3/2014 | Bornzin |
| 8,700,181 B2 | 4/2014 | Bornzin et al. |
| 8,721,587 B2 | 5/2014 | Berthiaume et al. |
| 8,727,996 B2 | 5/2014 | Allan et al. |
| 8,738,147 B2 | 5/2014 | Hastings et al. |
| 8,755,909 B2 | 6/2014 | Sommer |
| 8,758,365 B2 | 6/2014 | Bonner et al. |
| 9,119,959 B2 | 9/2015 | Rys |
| 9,155,882 B2 | 10/2015 | Grubac |
| 9,283,381 B2 | 3/2016 | Grubac |
| 9,414,857 B2 | 8/2016 | Wood |
| 9,446,248 B2 | 9/2016 | Sheldon |
| 9,526,522 B2 | 12/2016 | Wood et al. |
| 9,526,891 B2 | 12/2016 | Eggen |
| 9,539,423 B2 | 1/2017 | Bonner |
| 10,071,243 B2 | 9/2018 | Kuhn et al. |
| 10,099,050 B2 | 10/2018 | Chen et al. |
| 10,463,853 B2 | 11/2019 | Drake et al. |
| 10,518,084 B2 | 12/2019 | Kuhn et al. |
| 2002/0103424 A1 | 1/2002 | Swoyer et al. |
| 2002/0077556 A1 | 6/2002 | Schwartz |
| 2002/0095203 A1 | 7/2002 | Thompson |
| 2002/0165589 A1 | 11/2002 | Imran et al. |
| 2003/0004537 A1 | 1/2003 | Boyle et al. |
| 2003/0088301 A1 | 5/2003 | King |
| 2003/0233139 A1 | 12/2003 | Chitre et al. |
| 2004/0034401 A1 | 2/2004 | Dahlberg |
| 2004/0147973 A1 | 7/2004 | Hauser |
| 2004/0176797 A1 | 9/2004 | Opolski |
| 2004/0230280 A1 | 11/2004 | Cates |
| 2004/0230281 A1 | 11/2004 | Heil et al. |
| 2004/0249417 A1 | 12/2004 | Ransbury et al. |
| 2005/0090890 A1 | 4/2005 | Wu et al. |
| 2005/0267555 A1 | 12/2005 | Marnfeldt et al. |
| 2006/0084965 A1 | 4/2006 | Young |
| 2006/0085039 A1 | 4/2006 | Hastings et al. |
| 2006/0085041 A1 | 4/2006 | Hastings et al. |
| 2006/0247753 A1 | 11/2006 | Wenger |
| 2007/0043414 A1 | 2/2007 | Fifer et al. |
| 2007/0043441 A1 | 2/2007 | Fifer et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0233218 A1 | 10/2007 | Kolberg |
| 2007/0239248 A1 | 10/2007 | Hastings et al. |
| 2007/0255376 A1 | 11/2007 | Michels et al. |
| 2007/0276444 A1 | 11/2007 | Gelbart |
| 2007/0293904 A1 | 12/2007 | Gelbart |
| 2008/0021532 A1 | 1/2008 | Kveen et al. |
| 2008/0051863 A1 | 2/2008 | Schneider |
| 2009/0082827 A1 | 3/2009 | Kveen et al. |
| 2009/0082828 A1 | 3/2009 | Ostroff |
| 2009/0204170 A1 | 8/2009 | Hastings et al. |
| 2009/0281605 A1 | 11/2009 | Marnfeldt et al. |
| 2010/0131036 A1 | 5/2010 | Geistert et al. |
| 2010/0198288 A1 | 8/2010 | Ostroff |
| 2010/0211149 A1 | 8/2010 | Morgan et al. |
| 2011/0034939 A1 | 2/2011 | Kveen et al. |
| 2011/0054555 A1 | 3/2011 | Williams et al. |
| 2011/0112548 A1 | 5/2011 | Fifer et al. |
| 2011/0125163 A1 | 5/2011 | Rutten et al. |
| 2011/0190785 A1 | 8/2011 | Gerber et al. |
| 2011/0190786 A1 | 8/2011 | Gerber et al. |
| 2011/0208260 A1 | 8/2011 | Jacobson |
| 2011/0237967 A1 | 9/2011 | Moore et al. |
| 2011/0251660 A1 | 10/2011 | Griswold |
| 2011/0251661 A1 | 10/2011 | Fifer |
| 2011/0251662 A1 | 10/2011 | Griswold et al. |
| 2011/0270339 A1 | 11/2011 | Murray, III et al. |
| 2011/0270340 A1 | 11/2011 | Pellegrini |
| 2011/0282423 A1 | 11/2011 | Jacobson |
| 2011/0307043 A1 | 12/2011 | Ollivier |
| 2012/0078322 A1 | 3/2012 | Dal Molin et al. |
| 2012/0078336 A1 | 3/2012 | Helland |
| 2012/0095539 A1 | 4/2012 | Khairkhahan et al. |
| 2012/0108986 A1 | 5/2012 | Beasley |
| 2012/0109002 A1 | 5/2012 | Mothilal et al. |
| 2012/0109079 A1 | 5/2012 | Asleson et al. |
| 2012/0109148 A1 | 5/2012 | Bonner et al. |
| 2012/0109149 A1 | 5/2012 | Bonner et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson |
| 2012/0172891 A1 | 7/2012 | Lee |
| 2012/0172892 A1 | 7/2012 | Grubac |
| 2012/0197373 A1 | 8/2012 | Khairkhahan et al. |
| 2012/0232565 A1 | 9/2012 | Kveen et al. |
| 2012/0271134 A1 | 10/2012 | Allan et al. |
| 2012/0330392 A1 | 12/2012 | Regnier et al. |
| 2013/0006261 A1 | 1/2013 | Lampropoulos et al. |
| 2013/0006262 A1 | 1/2013 | Lampropoulos et al. |
| 2013/0012925 A1 | 1/2013 | Berthiaume et al. |
| 2013/0035636 A1 | 2/2013 | Beasley et al. |
| 2013/0035748 A1 | 2/2013 | Bonner et al. |
| 2013/0053921 A1 | 2/2013 | Bonner et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0103049 A1 | 4/2013 | Bonde |
| 2013/0110127 A1 | 5/2013 | Bornzin |
| 2013/0110219 A1 | 5/2013 | Bornzin et al. |
| 2013/0116738 A1 | 5/2013 | Samade |
| 2013/0116740 A1 | 5/2013 | Bornzin et al. |
| 2013/0116741 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0233345 A1 | 9/2013 | Baarsch et al. |
| 2013/0253342 A1 | 9/2013 | Griswold et al. |
| 2013/0253343 A1 | 9/2013 | Waldhauser et al. |

(56) References Cited

U.S. PATENT DOCUMENTS

| | | |
|---|---|---|
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0296957 A1 | 11/2013 | Tronnes |
| 2013/0331940 A1* | 12/2013 | Swanick ............... A61F 2/0063 623/11.11 |
| 2014/0058494 A1 | 2/2014 | Ostroff et al. |
| 2014/0074114 A1 | 3/2014 | Khairkhahan et al. |
| 2014/0107723 A1 | 4/2014 | Hou |
| 2014/0148815 A1 | 5/2014 | Wenzel et al. |
| 2014/0180306 A1 | 6/2014 | Grubac |
| 2015/0039069 A1 | 2/2015 | Rys et al. |
| 2015/0039070 A1 | 2/2015 | Kuhn |
| 2015/0039071 A1 | 2/2015 | Grubac |
| 2015/0051616 A1 | 2/2015 | Haasl et al. |
| 2015/0051682 A1 | 2/2015 | Schmidt |
| 2015/0094668 A1 | 4/2015 | Wood et al. |
| 2015/0352353 A1 | 12/2015 | Rys |
| 2016/0001068 A1 | 1/2016 | Grubac et al. |
| 2016/0059002 A1* | 3/2016 | Grubac ................. A61N 1/057 606/129 |
| 2016/0094668 A1 | 3/2016 | Chang et al. |
| 2017/0209688 A1 | 7/2017 | Drake et al. |
| 2017/0209689 A1* | 7/2017 | Chen ................... A61N 1/0573 |
| 2018/0071543 A1* | 3/2018 | Taff ..................... A61N 1/3756 |

FOREIGN PATENT DOCUMENTS

| | | |
|---|---|---|
| CN | 1882370 A | 12/2006 |
| DE | 2053919 A1 | 5/1972 |
| EP | 0212955 A2 | 3/1987 |
| EP | 779080 | 5/2003 |
| JP | 0288666 | 7/1990 |
| JP | 05245215 A | 9/1993 |
| RU | 2011151104 | 6/2013 |
| WO | 95/20993 A2 | 8/1995 |
| WO | 01/02053 A1 | 1/2001 |
| WO | 2002022202 A2 | 3/2002 |
| WO | WO 03032807 A1 | 4/2003 |
| WO | WO 2004028348 A2 | 4/2004 |
| WO | 2006118865 A2 | 11/2006 |
| WO | WO 200903 9400 A1 | 3/2009 |
| WO | WO 2009042295 A1 | 4/2009 |
| WO | WO 2010131157 A1 | 11/2010 |
| WO | WO 2012092067 A1 | 7/2012 |
| WO | WO 2012092074 A1 | 7/2012 |
| WO | 2012/135530 A1 | 10/2012 |
| WO | WO 2014006471 A1 | 1/2014 |
| WO | 2015017234 A1 | 2/2015 |
| WO | 2015017273 A1 | 2/2015 |
| WO | 2017127689 A1 | 7/2017 |
| WO | 2017127695 A1 | 7/2017 |
| WO | 2018081363 A1 | 5/2018 |

OTHER PUBLICATIONS

Non-Final Office Action from U.S. Appl. No. 16/158,724, dated Oct. 6, 2020, 7 pp.
International Search Report and Written Opinion of International Application No. PCT/US2020/024582, dated Jul. 7, 2020, 8 pp.
Prosecution History from U.S. Appl. No. 16/158,724, dated Jul. 8, 20120 through Jan. 4, 2021, 47 pp.
"Homer Mammalok Gold," accessed on or about Jan. 19, 2017, accessed from http://www.mana-tech.com/factsheets/HomerMammalok. pdf, 1 pp.
Medtronic model SELECTRSURE™ 3830 manual, 2013, accessed on or about Jan. 19, 2017, 20 pp.
Merriam-Webster Definition of "Compound Curve," accessed on Apr. 25, 2017, https://merriam-webster.com/dictionary/compound%20curve, 4 pp.
Prosecution History from U.S. Appl. No. 15/410,161, dated from Jan. 19, 2017 through Jun. 16, 2018, 31 pp.
Prosecution History from U.S. Appl. No. 16/158,724, dated from Oct. 12, 2018 through Nov. 29, 2018, 37 pp.
Spickler, et al., "Totally Self-Contained Intracardiac Pacemaker," J. Electrocardiology, vol. 3, Nos. 3 & 4, pp. 325-331, 1970. (Applicant points out, in accordance with MPEP 609.04(a), that the year of publication, 1970 is sufficiently earlier than the effective U.S. filing date, so that the particular month of publication is not in issue.).
U.S. Appl. No. 16/158,724, filed by Xin Chen et al., filed Oct. 12, 2018.
First Office Action and Search Report, and translation thereof, from Chinese Application No. 201780018926.5, dated Jun. 25, 2021, 13 pp.
Haqqani et al., "The Implantable Cardioverter-Defibrillator Lead: Principles, Progress and Promises," PACE, vol. 32, Oct. 2009, pp. 1336-1353.
Tjong et al., "Acute and 3-Month Performance of a Communicating Leadless Antitachycardia Pacemaker and Subcutaneous Implantable Defibrillator," JACC: Clinical Electrophysiology, vol. 3, No. 13, Dec. 26, 2017, pp. 1487-1498.
Tjong et al., "The modular cardiac rhythm management system: the EMPOWER leadless pacemaker and the EMBLEM subcutaneous ICD," Herzschrittmachertherapie + Elektrophysiologie, vol. 29, Oct. 31, 2018, pp. 355-361.

* cited by examiner

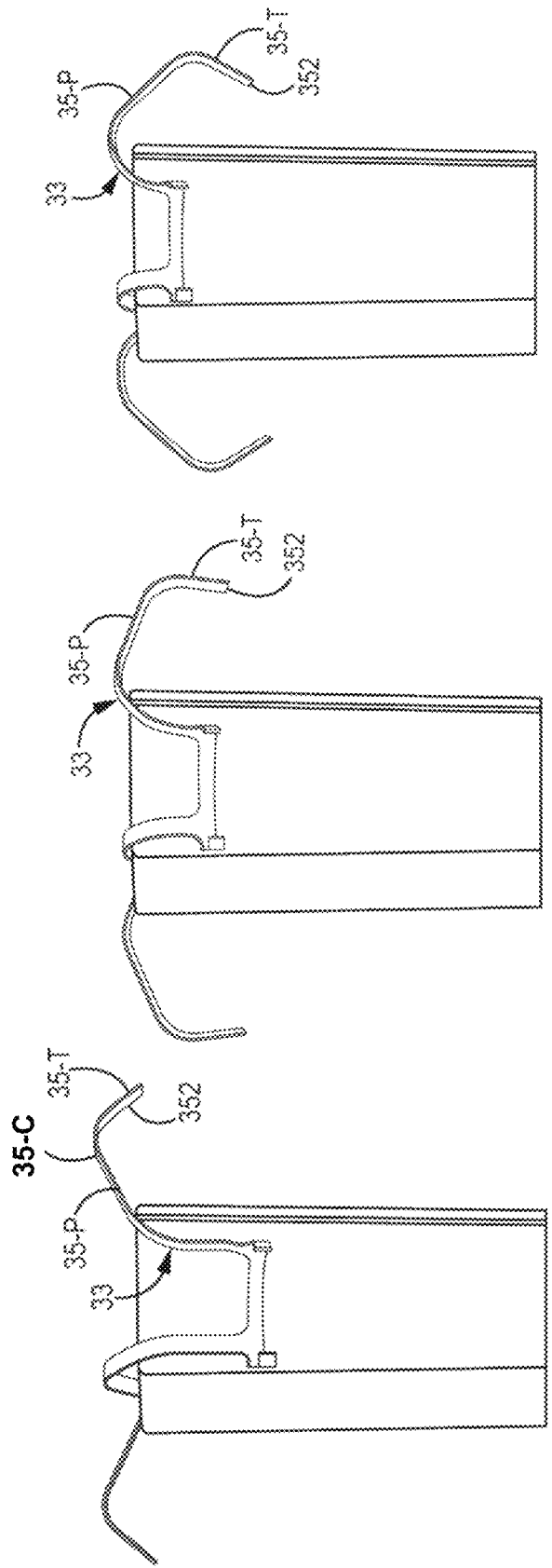

FIXATION COMPONENTS FOR IMPLANTABLE MEDICAL DEVICES

The present application claims benefit of U.S. Provisional Patent Application No. 62/825,233, filed Mar. 28, 2019, entitled FIXATION COMPONENTS FOR IMPLANTABLE MEDICAL DEVICES, which is incorporated herein by reference in its entirety.

TECHNICAL FIELD

This disclosure is related to medical device systems, such as relatively compact implantable medical devices and associated fixation components.

BACKGROUND

In some examples, implantable cardiac pacemakers include a pulse generator device to which one or more flexible elongate lead wires are coupled. The pulse generator device may be implanted in a subcutaneous pocket, remote from the heart, and each of the one or more lead wires extends therefrom to a corresponding electrode, coupled thereto and positioned at a pacing site, either endocardial or epicardial. Mechanical and/or MRI compatibility issues may be associated with elongate lead wires. Relatively compact implantable medical devices (IMDs) have been developed that are wholly contained within a relatively compact package, the entirety of which is configured for implant in close proximity to the pacing site, e.g., within a chamber of the heart.

SUMMARY

This disclosure describes IMD fixation components having improved flexibility, fixation, or both to facilitate implanting IMDs, including relatively compact IMDs. A fixation component of an IMD may include a plurality of tines. Each respective tine of the plurality of tines has a deployment stiffness that enables the respective tine to penetrate the tissue at a target implant site. By controlling the deployment stiffness, the plurality of tines may have improved tissue fixation, including, for example, controlling of a depth of tine penetration and an amount of tissue engagement in a lateral direction. Each respective tine of the plurality of tines also has a deflection stiffness that may enable a clinician to confirm adequate fixation of the tines into the tissue of the patient. For example, a pull test or tug test may be performed under fluoroscopy to confirm that the plurality of tines have engaged the tissue. By controlling the deflection stiffness, the plurality of tines may have an improved flexibility that enables a clinician to more easily confirm tissue engagement.

In some examples, a fixation component for an implantable medical device (IMD) may include a base defining a longitudinal axis of the fixation component and a plurality of tines extending from the base and being spaced apart from one another. The base may be fixedly attached to the IMD having a proximal end and a distal end aligned along the longitudinal axis. Each tine of the plurality of tines may include a proximal portion and a distal portion. The Proximal portion may include a proximal section fixedly attached to the base and extending from the base in a first direction; a first curved section defining a first deformable pre-formed curvature and extending from the proximal section laterally, outward from the longitudinal axis; a first straight section extending from the first curved section laterally, outward from the longitudinal axis in a second direction; and a second curved section defining a second deformable pre-formed curvature and extending from the first straight section laterally, outward from the longitudinal axis. The distal portion may include a second straight section extending from the second curved section in a third direction oriented generally opposite the first direction; a third curved section defining a third deformable pre-formed curvature and extending from the second straight section; and tip section extending from the third curved section toward the longitudinal axis and terminating in a free distal end.

In some examples, a fixation component for an implantable medical device (IMD), may include a base defining a longitudinal axis of the fixation component and a plurality of tines extending from the base and being spaced apart from one another. The base may be fixedly attached to the IMD having a proximal end and a distal end aligned along the longitudinal axis. Each tine of the plurality of tines may include a proximal portion and a distal portion. The proximal portion may include a proximal section fixedly attached to the base and extending in a first direction generally parallel to the longitudinal axis; and a first curved section extending from the proximal section laterally, outward from the longitudinal axis, wherein the curved section is configured to provide a deflection stiffness of less than about 0.6 Newtons. The distal portion may include a second proximal section extending from the first curved section in a second direction oriented generally opposite the first direction; a second curved section having a deformable pre-formed curve and extending from the second proximal section; and tip section extending from the second curved section toward the longitudinal axis and terminating in a free distal end.

In some examples, an implantable medical device (IMD) may include a housing extending along a longitudinal axis from a proximal end to a distal end; an electrode mounted in proximity to the distal end of the housing; and a fixation component. The fixation component may include a base in proximity to the distal end of the housing and a plurality of tines fixedly attached spaced from one another around a perimeter of the distal end of the housing. Each tine of the plurality of tines may include a proximal portion and a distal portion. The proximal portion may include a proximal section fixedly attached to the base and extending from the base in a first direction; a first curved section defining a first deformable pre-formed curvature and extending from the proximal section laterally, outward from the longitudinal axis; a first straight section extending from the first curved section laterally, outward from the longitudinal axis in a second direction; and a second curved section defining a second deformable pre-formed curvature and extending from the first straight section laterally, outward from the longitudinal axis. The distal portion may include a second straight section extending from the second curved section in a third direction oriented generally opposite the first direction; a third curved section defining a third deformable pre-formed curvature and extending from the second straight section; and tip section extending from the third curved section toward the longitudinal axis and terminating in a free distal end.

In some examples, a medical device system may include an implantable medical device (IMD) including a housing extending along a longitudinal axis from a proximal end to a distal end; an electrode mounted in proximity to the distal end of the housing; and a fixation component that includes a base in proximity to the distal end of the housing and a plurality of tines fixedly attached spaced from one another around a perimeter of the distal end of the housing; and a delivery tool including a tubular sidewall that defines a lumen into which the IMD may be loaded, wherein the lumen having a distal opening through which the IMD may be deployed. Each tine of the plurality of tines including a proximal portion that includes a proximal section fixedly attached to the base and extending from the base in a first direction; a first curved section defining a first deformable pre-formed curvature and extending from the proximal section laterally, outward from the longitudinal axis; a first straight section extending from the first curved section laterally, outward from the longitudinal axis in a second direction; and a second curved section defining a second deformable pre-formed curvature and extending from the first straight section laterally, outward from the longitudinal axis; and a distal portion that includes a second straight section extending from the second curved section in a third direction oriented generally opposite the first direction; a third curved section defining a third deformable pre-formed curvature and extending from the second straight section; and tip section extending from the third curved section toward the longitudinal axis and terminating in a free distal end.

In some examples, a method of forming a fixation component for an IMD may include forming a base defining a longitudinal axis of the fixation component; and forming a plurality of tines extending from the base and being spaced apart from one another. Each tine of the plurality of tines may include a proximal portion including a proximal section fixedly attached to the base and extending from the base in a first direction; a first curved section defining a first deformable pre-formed curvature and extending from the proximal section laterally, outward from the longitudinal axis; a first straight section extending from the first curved section laterally, outward from the longitudinal axis in a second direction; and a second curved section defining a second deformable pre-formed curvature and extending from the first straight section laterally, outward from the longitudinal axis; and a distal portion including a second straight section extending from the second curved section in a third direction oriented generally opposite the first direction; a third curved section defining a third deformable pre-formed curvature and extending from the second straight section; and tip section extending from the third curved section toward the longitudinal axis and terminating in a free distal end.

The details of one or more examples are set forth in the accompanying drawings and the description below. Other features, objects, and advantages will be apparent from the description and drawings, and from the claims.

BRIEF DESCRIPTION OF DRAWINGS

FIG. 7D is a conceptual diagram illustrating further movement of the fixation component as the portions of the tines between the distal most and next proximal curves reaches the distal end of the delivery tool.

FIG. 7E is a conceptual diagram illustrating further movement fixation component as the proximal curve travels past the distal end of the delivery tool.

FIG. 7F is a conceptual diagram illustrating final configuration of fixation component movement, subsequent to movement.

DETAILED DESCRIPTION

Figure 1:
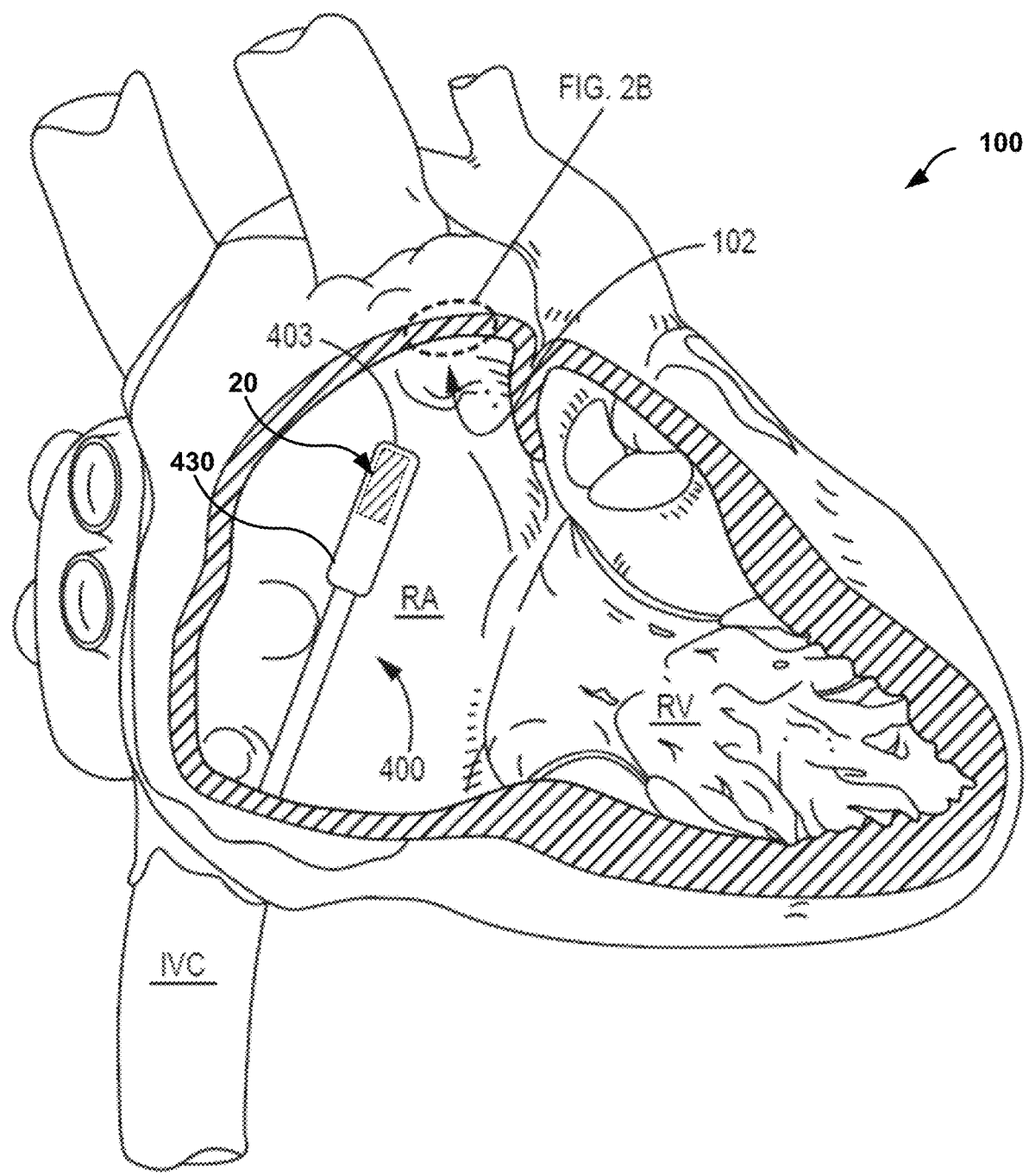
FIG. 1 is a conceptual diagram illustrating a portion of an example medical device system configured to implant a relatively compact IMD at a target implant site.

This disclosure describes IMD fixation components having improved flexibility, fixation, or both to facilitate implanting IMDs, such as relatively compact IMDs. An example fixation component for an IMD may include a base and a plurality of tines. The plurality of tines is configured be deployed with a target deployment stiffness to engage tissue a target implant site while maintaining a target deflection stiffness after deployment to enable visualization (e.g., via fluoroscopy) of engagement with the tissue. The base may define a longitudinal axis of the fixation component, e.g., a proximal end and a distal end of the IMD may be aligned along the longitudinal axis. The base may be fixedly attached to the IMD near the distal end of the IMD. The plurality of tines may be spaced apart from one another around a perimeter of the distal end of the IMD and extend from the base. A shape of each respective tine of the plurality of tines may be selected to control each of the target deployment stiffness and target deflection stiffness. For example, the shape of a respective tine may include a number of preformed curves on the respective tine, a curvature (e.g., radius) of each preformed curve on the respective tine, a length of each preformed curve, a length of straight sections between preformed curves, a width of the respective tine or sections thereof (e.g., one or more tapered portions), a thickness of the respective tine, a number of cutouts along the length of the respective tine, shapes of cutouts, or any combination thereof.

Each tine of the plurality of tines may include a proximal portion and a distal portion. The proximal portion may include a proximal section and at least one curved section. In some examples, the proximal portion may include a curved section. In some examples, the proximal portion may include a first curved section, a second curved section, and a first straight section between the first and second curved sections. The proximal section is fixedly attached to the base and extends from the base in a first direction. For example, the first direction may be substantially parallel (e.g., parallel or nearly parallel within the capabilities of fixation component manufacturing techniques) to the longitudinal axis or at some angle relative to the longitudinal axis. The first curved section may define a first deformable pre-formed curvature and extend from the proximal section laterally, outward from the longitudinal axis. The first straight section extends from the first curved section laterally, outward from the longitudinal axis in a second direction. The second curved section defines a second deformable pre-formed curvature and extends from the first straight section laterally, outward from the longitudinal axis. The distal portion may include a second straight section extending from the second curved section in a third direction oriented generally opposite the first direction, a third curved section defining a third deformable pre-formed curvature and extending from the second straight section, and tip section extending from the third curved section toward the longitudinal axis and terminating in a free distal end.

When deployed at a target implant site, the tines have a deployment stiffness that enables a respective tine to penetrate the tissue at a target implant site. By controlling the deployment stiffness, the tines may have improved tissue fixation, including control of a depth of tine penetration and an amount of tissue engagement in a lateral direction. After deployment at the target implant site, a deflection stiffness of the tines enables a clinician to confirm adequate fixation of the tines into tissue of a patient. For example, a pull test or tug test may be performed under fluoroscopy to confirm that the tines have engaged the tissue to confirm adequacy of implantation of the IMD. The pull test or tug test may include the clinician pulling or tugging on the deployed IMD and observing movement of the tines to determine if the tines are engaged in tissue, e.g., the tines that are embedded in tissue deflect or bend as deployed IMD is pulled or tugged. By controlling the deflection stiffness, the tines may have an improved flexibility that enables a clinician to more easily confirm tissue engagement.

In this disclosure, the example systems, devices, and techniques will be described with reference to delivering an IMD to a target site in a heart of a patient. However, it will be understood that example systems, devices, and techniques of the present disclosure are not limited to delivering IMDs to a target site in the heart. For example, example systems, devices, and techniques described herein may be used to deliver other medical devices, such as drug delivery device, sensing devices, neurostimulation device, or medical electrical leads to other locations within a body of a patient. In short, the example systems, devices, and techniques described herein can find useful application in delivery of a wide variety of implantable medical devices for delivery of therapy to a patient or patient sensing.

FIG. 1 is a conceptual diagram illustrating a portion of an example medical device system 400 configured to implant a relatively compact implantable medical device 20 ("IMD 20") at a target implant site 102. In some examples, as illustrated in FIG. 1, the target implant site 102 may include an appendage of a right atrium RA of the heart 100 of a patient. In some examples, target implant site 102 may include other portions of heart 100 or other locations within a body of the patient. Medical device system 400 may include a delivery tool 430 configured to house and controllably deploy relatively compact IMD 20. In some examples, a clinician may maneuver medical device system 400 to target implant site 102. For example, with the IMD 20 loaded therein, the clinician may guide delivery tool 430 up through the inferior vena cava IVC and into the right atrium RA. In some examples, other pathways or techniques may be used to guide delivery tool 430 into other target implant sites within the body of the patient.

Figure 2A:
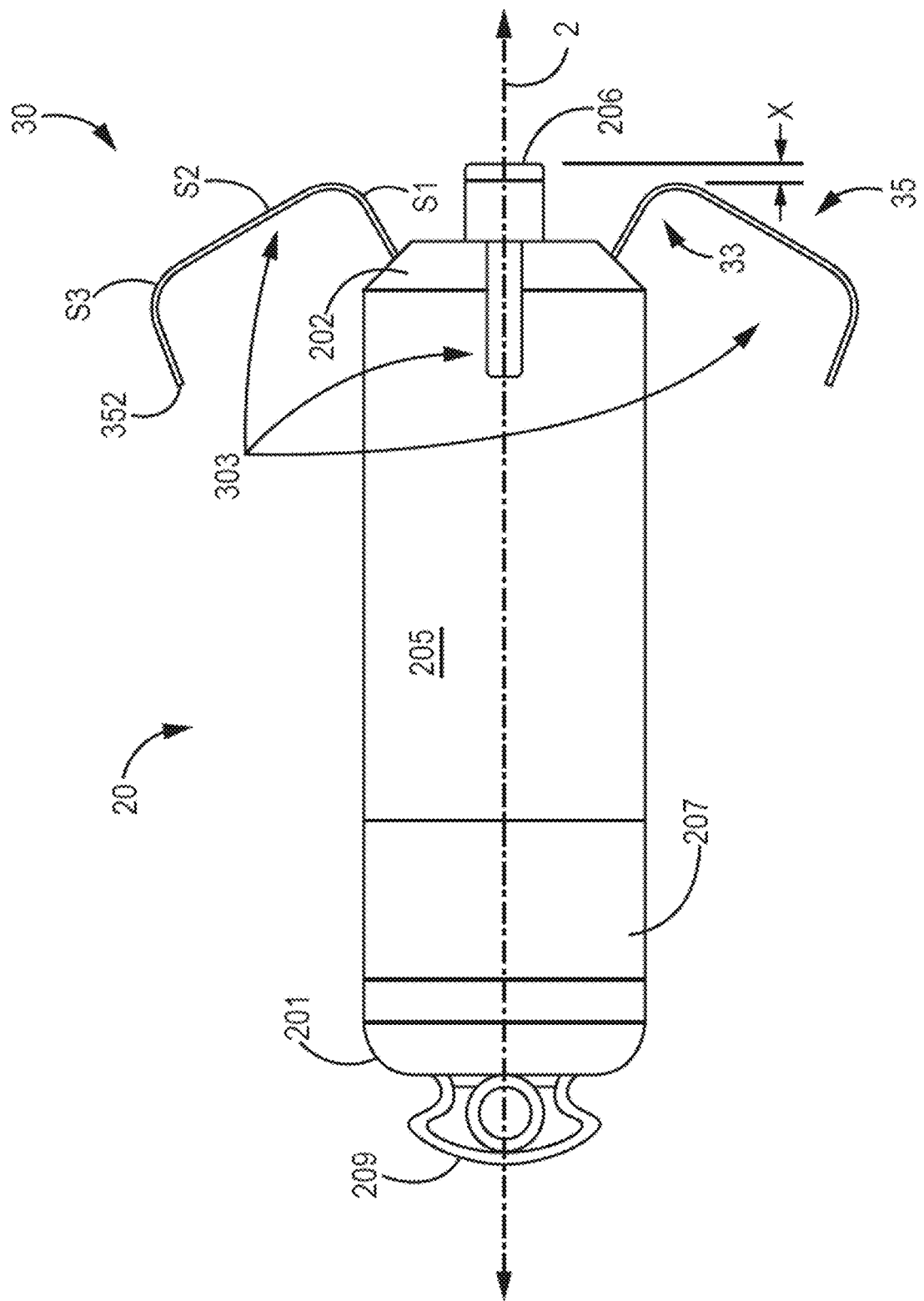
FIG. 2A is a conceptual diagram illustrating a plan view of a relatively compact IMD including a fixation component.

FIG. 2A is a conceptual diagram illustrating a plan view of a relatively compact IMD 20 including a fixation component 30. IMD 20 includes housing 205 extending along longitudinal axis 2 from a proximal end 201 to a distal end 202. Housing 205 may be formed from a biocompatible and biostable metal such as titanium. In some examples, housing 205 may include a hermetically sealed housing. IMD 20 may include any suitable dimensions. In some examples, an outer diameter of IMD 20 (e.g., outer diameter of housing 205) may be between about 10 French and about 30 French, such as about 20 French.

IMD 20 may contain electronic circuitry, including one or more of sensing circuitry (e.g., for sensing cardiac signals), therapy delivery circuitry (e.g., for generating cardiac pacing pulses), and processing circuitry for controlling the functionality of IMD 20, and may include an electrode 206. The electronic circuitry may be configured to generate and deliver an electrical pulse therapy to tissue proximate electrode 206. Electrode 206 may be spaced apart from distal end 202 of housing 205, for example, being coupled to the sensing and therapy delivery circuitry by a conductor of an hermetic feedthrough assembly (not shown). In some examples, IMD 20 includes a holding member 209 fixedly attached to proximal end 201 of housing 205, wherein holding member 209 is configured for temporarily tethering IMD 20 to a delivery tool, such as delivery tool 430. Housing 205 may be overlaid with an insulative layer, for example, medical grade polyurethane, parylene, or silicone. The insulative layer may define second electrode 207, for example, by removing a portion of the insulative layer to expose the metallic surface of housing 205. Electrode 206 may function in conjunction with second electrode 207 for bipolar pacing and sensing.

Fixation component 30 includes a plurality of tines 303 ("tines 303"). Tines 303 may be configured to hold electrode 206 in contact with tissue at a target implant site, e.g., target implant site 102. In some examples, electrode 206 may longitudinally be approximately flush with a distal-most portion of tines 303 (e.g., relative to longitudinal axis 2), or distal thereto by a distance "X" that may be up to about 2 millimeters (mm). Tines 303 include a proximal portion 33 and a distal portion 35. Each of proximal portion 33 and distal portion 35 may include one or more sections. For example, as illustrated in FIG. 2A, tines 303 may include first section S1, second section S2, and third section S3. In other examples, tines 303 may include fewer section, such as two sections, or more sections, such as more than three sections. Each of first, second, and third section S1, S2, and S3 may include an elastically deformable material preformed into a curved section and/or a substantially straight section. In the example illustrated in FIG. 2A, first section S1 is fixedly attached to distal end 202 of device housing 205 and extends around a pre-formed curvature to second section S2. Second section S2 extends proximally along a relatively straight line to third section S3. Third section S3 extending around a pre-formed curvature to a free distal end 352.

Tines 303 may be configured to have a target deflection stiffness and a target deployment stiffness. The target deflection stiffness may include a measure of a resistance to force applied to IMD 20 in a proximal direction when fixation component 30 is engaged with tissue at target site 102. In some examples, the target deflection stiffness may be selected to enable tines 303 to deflect a predetermined amount to enable visualization of tines 303 under fluoroscopy. In some examples, the target deflection stiffness may be within a range from about 0.2 N to about 0.8 N, such as about 0.3 N to about 0.6 N. The deployment stiffness may include a measure of a force applied by tines 303 as tines 303 move from a deformed configuration to an undeformed configuration upon deployment of fixation component 30 from distal opening 403 of delivery tool 430 (FIG. 1) such that free distal end 352 penetrates pectinate muscle PM. In some examples, the target deployment stiffness may be within a range from about 0.6 N to about 1.2 N.

Figure 2B:
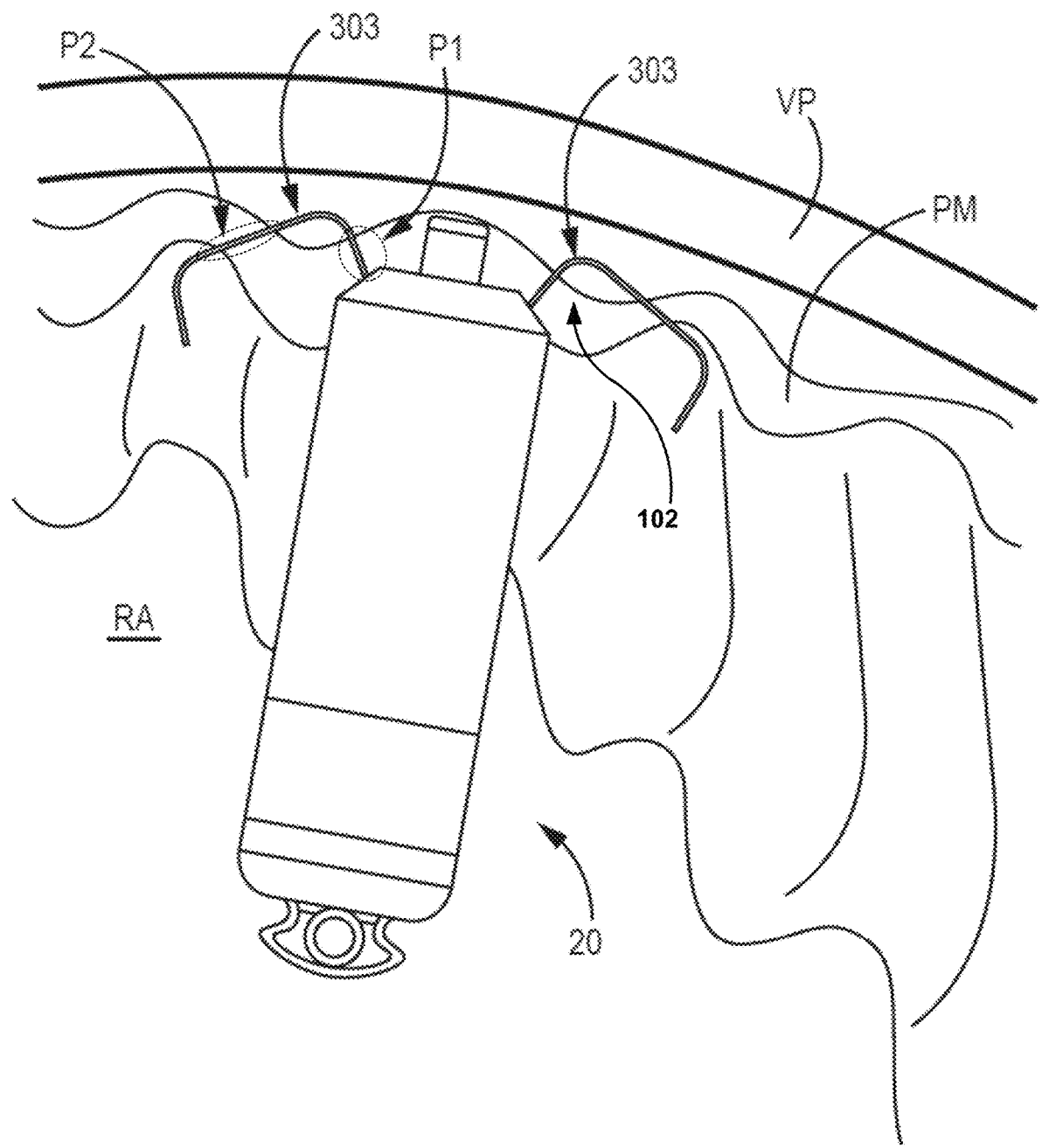
FIG. 2B is a conceptual diagram illustrating the IMD of FIG. 2A implanted at a target implant site.

FIG. 2B is a conceptual diagram illustrating IMD 20 implanted at target implant site 102. Target implant site 102 includes a portion the right atrial RA wall having a laminate structure that includes an inner layer of pectinate muscle PM and an outer layer of visceral pericardium VP, which forms the epicardial surface. IMD 20 is secured at target implant site 102 by tines 303 of fixation component 30 penetrating through the layer of pectinate muscle PM without perforating through visceral pericardium VP. Perforation of the visceral pericardium VP may result in pericardial effusion. Tines 303 are configured for spring-loaded release, upon deployment out through distal opening 403 of delivery tool 430 (FIG. 1) such that free distal end 352 penetrates pectinate muscle PM without perforating visceral pericardium VP. It should be noted that alternate suitable implant sites for embodiments of fixation member tines described herein can be along any endocardial surface defined by pectinate muscle PM.

Figure 3A:
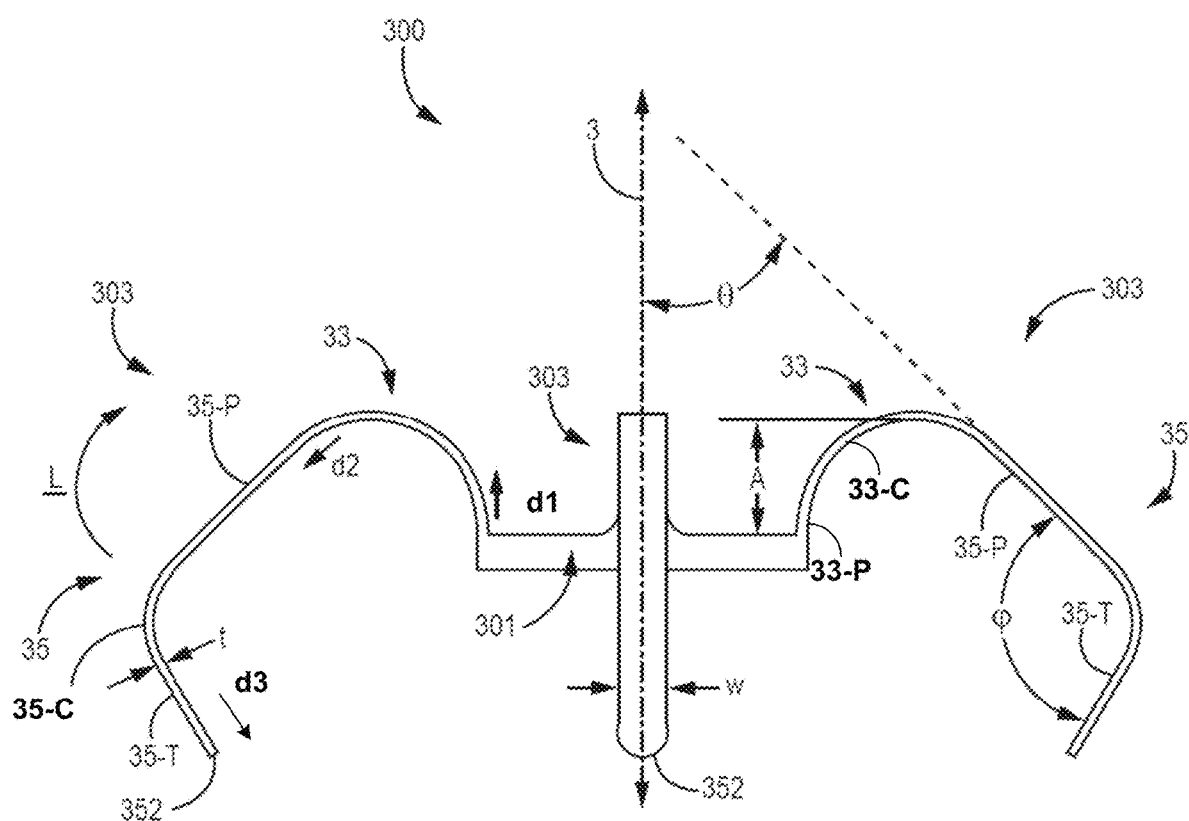
FIG. 3A is a conceptual diagram illustrating an elevation view of an example two-knuckle fixation component.
Figure 3B:
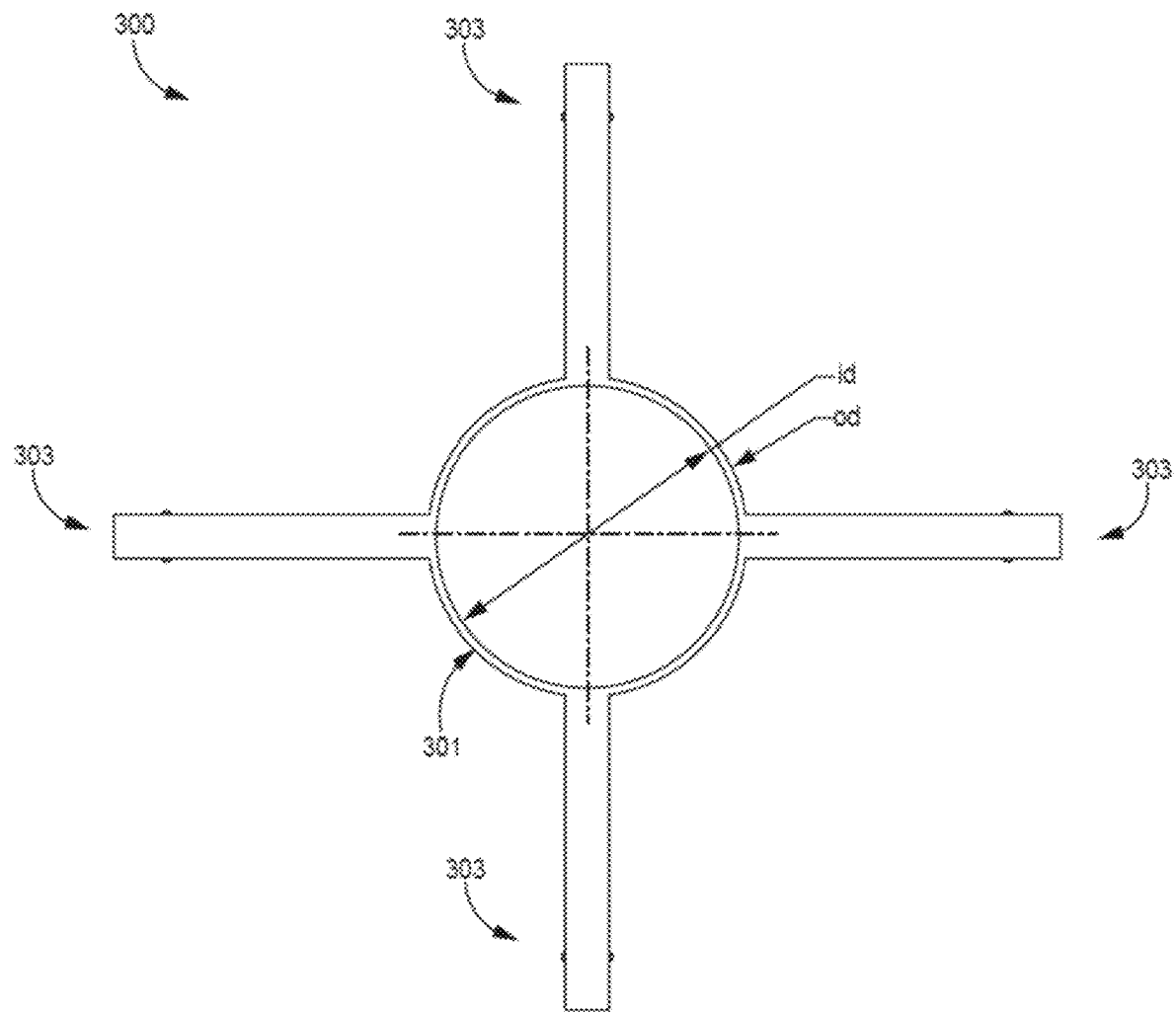
FIG. 3B is a conceptual diagram illustrating an end view of the two-knuckle fixation component of FIG. 3A.

FIG. 3A is a conceptual diagram illustrating an elevation view of an example two-knuckle fixation component 300. FIG. 3B is a conceptual diagram illustrating an end view of fixation component 300 of FIG. 3A. Two-knuckle fixation component 300 may be the same as or substantially similar to fixation component 30, except for the differences described herein. For example, two-knuckle fixation component 300 includes tines 303. Tines 303 are illustrated in a relaxed configuration, e.g., a configuration without application of any external forces on any portion of tines 303. Fixation component 300 is referred to as a two-knuckle fixation component because it has two curved sections resulting two knuckles.

As illustrated in FIG. 3A, two-knuckle fixation component 300 includes a base 301 from which tines 303 extend. Base 301 may define a longitudinal axis 3 of two-knuckle fixation component 300. When base 301 is mounted around distal end 202 of device housing 205 such that a perimeter of two-knuckle fixation component 300 extends around electrode 206, longitudinal axis 3 is generally aligned along longitudinal axis 2 of IMD 20 (FIG. 2A).

As illustrated in FIG. 3B, tines 303 are spaced apart from one another around a perimeter of base 301. Base 301 may have an inner diameter ("id") of about 0.20 inch (5.08 millimeters, mm) and an outer diameter od of about 0.21 inch (5.334 mm). In some examples, two-knuckle fixation component 300 may be mounted to distal end 202 of device housing 205, for example, in a manner the same or substantially similar to that described in commonly assigned U.S. Pat. No. 10,099,050B2 (filed on Jan. 19, 2017), which is incorporated herein by reference in its entirety. In some examples, two-knuckle fixation component 300 may include separately formed tines 303 that are individually mounted to distal end 202 of device housing 205 (e.g., not integrated together with base 301).

Tines 330 may include any suitable elastically deformable biocompatible material. In some examples, tines 303 may include a super-elastic material, such as, for example, a nickel-titanium alloy. For example, two-knuckle fixation component 300 may be cut from a medical grade nickel-titanium alloy tubing that conforms to the chemical, physical, mechanical, and metallurgical requirements of the ASTM F2063 standard, and has a wall thickness of about 0.005 inch (0.127 mm). In this way, tines 303 may be integrally formed with base 301 and each tine of tines 303 may have a constant thickness "t" of about 0.005 inch±0.001 inch (0.127 mm±0.0254 mm). In some examples, after cutting tines 303, tines 303 may be shaped into a preformed configuration by bending and holding tines 303, while heat treating according to methods known to those skilled in the art.

As illustrated in FIG. 3A, each tine of tines 303 includes proximal portion 33 (e.g., which may correspond to first section S1) and distal portion 35 (e.g., which may correspond to second section S2 and third section S3). In some examples, free distal end 352 may include any suitable shape, such as, for example, a rounded shape as illustrated in FIG. 3A or an incisive shape. Proximal section 33-P is fixedly attached to base 301. Proximal section 33-P extends in a first direction $d_1$. In some examples, first direction $d_1$ may be substantially parallel to longitudinal axis 3. In some examples, first direction $d_1$ may be at an angle relative to longitudinal axis 3, such as for example, between about 0 degrees to about 5 degrees. Curved section 33-C may include a spring-biased pre-formed curvature. Curved section 33-C extends from proximal section 33-P laterally, outward from longitudinal axis 3 to distal portion 35. In some examples, curved section 33-C may include a single radius within a range from about 0.06 inch (1.524 mm) to about 0.08 inch (2.032 mm), such as about 0.067 inch±0.010 inch (1.7018 mm±0.254 mm). In some examples, proximal portion 33 may include more than one curved section.

Distal portion 35 may include a proximal section 35-P, a curved section 35-C, and a tip section 35-T. Proximal section 35-P may include a substantially straight segment extending in a second direction $d_2$ and along a relatively straight line (dashed line). In some examples, a length of proximal section 35-P may be within a range from about 0.075 inch (1.905 mm) to about 0.125 inch (3.175 mm), such as about 0.100 inch±0.005 inch (2.54 mm±0.127 mm). Proximal section 35-P may be oriented by curved section 33-C such that second direction $d_2$ is generally opposite first direction $d_1$ and the relatively straight line intersects longitudinal axis 3 at an acute angle θ. In some examples, angle θ is between about 30 degrees and about 60 degrees, such as about 45 degrees. Curved section 35-C may include a deformable pre-formed curvature. Curved section 35-C extends from proximal section 35-P (in direction $d_2$) back toward longitudinal axis 3 to tip section 35-T. In some examples, curved section 35-C, when un-deformed, is defined by a single radius within a range from about 0.045 inch (1.143 mm) to about 0.055 inch (1.397 mm), such as about 0.05 inch±0.010 inch. Tip section 35-T may include a substantially straight segment extending in a third direction $d_3$ from curved section 35-C to free distal end 352. In some examples, a length of each tip section 35-T may be within a range from about 0.055 inch (1.397 mm) to about 0.075 inch (1.905 mm), such as about 0.064 inch±0.005 inch (1.6256 mm±0.127 mm). Tip section 35-T is shown oriented by curved section 35-C, when un-deformed, to extend toward longitudinal axis 3, such that tip section 35-T and proximal section 35-P are shown enclosing an angle φ. In some examples, angle φ may be greater than or equal to about 90 degrees, such as in a range from about 90 degrees to about 120 degrees.

The shape (e.g., undeformed configuration) and width of each tine 303, and, in some examples, the super-elastic stiffness properties of nickel-titanium alloy, provide a sufficient spring force and structural stiffness for tines 303 to engage tissue for the fixation of IMD 20 at an implant site when deployed by delivery tool 430, as described in greater detail below. With reference to FIG. 3A, each tine 303 has a width "W" in a range from about 0.020 inch (0.508 mm) to about 0.035 inch (0.889 mm), such as about 0.031 inch (0.7874 mm). In some examples, a width of tines 303 may be selected to provide a radiopaque density that facilitates fluoroscopic visualization during and after the implant procedure.

FIGS. 4A-4E are conceptual diagrams illustrating plan views of tines 450A-450E (collectively, tines 450) of the two-knuckle fixation component 300 illustrated in FIGS. 3A and 3B, prior to forming curves in the tine. Tines 450 may be the same as or substantially similar to tines 303 discussed above in reference to FIGS. 2A-3B, except for the differences described herein. For example, tines 450 may include a proximal portion 452 extending form base 451 and distal portion 454 extending from proximal portion 452. As indicated by the dashed lines indicating approximate boundaries of sections, proximal portion 452 may include a proximal section 456 and curved section 458, and distal portion 454 may include a proximal section 460, a curved section 462, and a tip section 464.

Figure 4A:
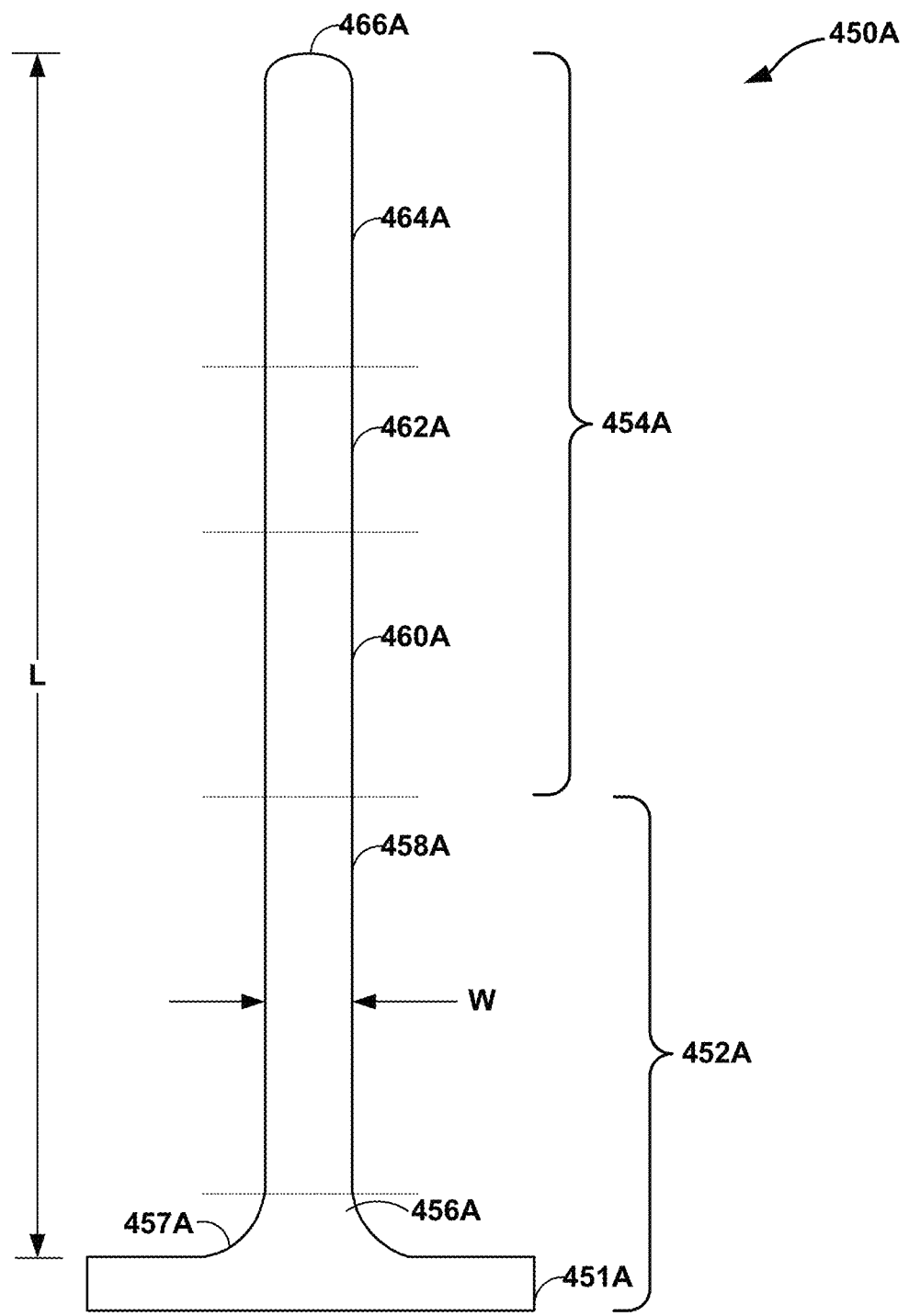
FIGS. 4A-4E are conceptual diagrams illustrating plan views of a tine of the two-knuckle fixation component of FIGS. 3A and 3B, prior to forming curves in the tine.

As illustrated in FIG. 4A, tine 450A may have a substantially constant width W (e.g., constant or nearly constant within the limits of common manufacturing tolerances) along the length L of tines 450A. For example, proximal portion 452A, including curved section 458A, and distal portion 454A, including proximal section 460A, a curved section 462A, and a tip section 464A, may have a substantially constant width. In some examples, proximal section 456A may include a fillet 457A extending from base 451A. Fillet 457A may reduce stress concentration at the junction of proximal section 456A and base 451A. The width W and length L of tine 450A may be the same as or substantially similar to tine 303 discussed above.

Figure 4B:
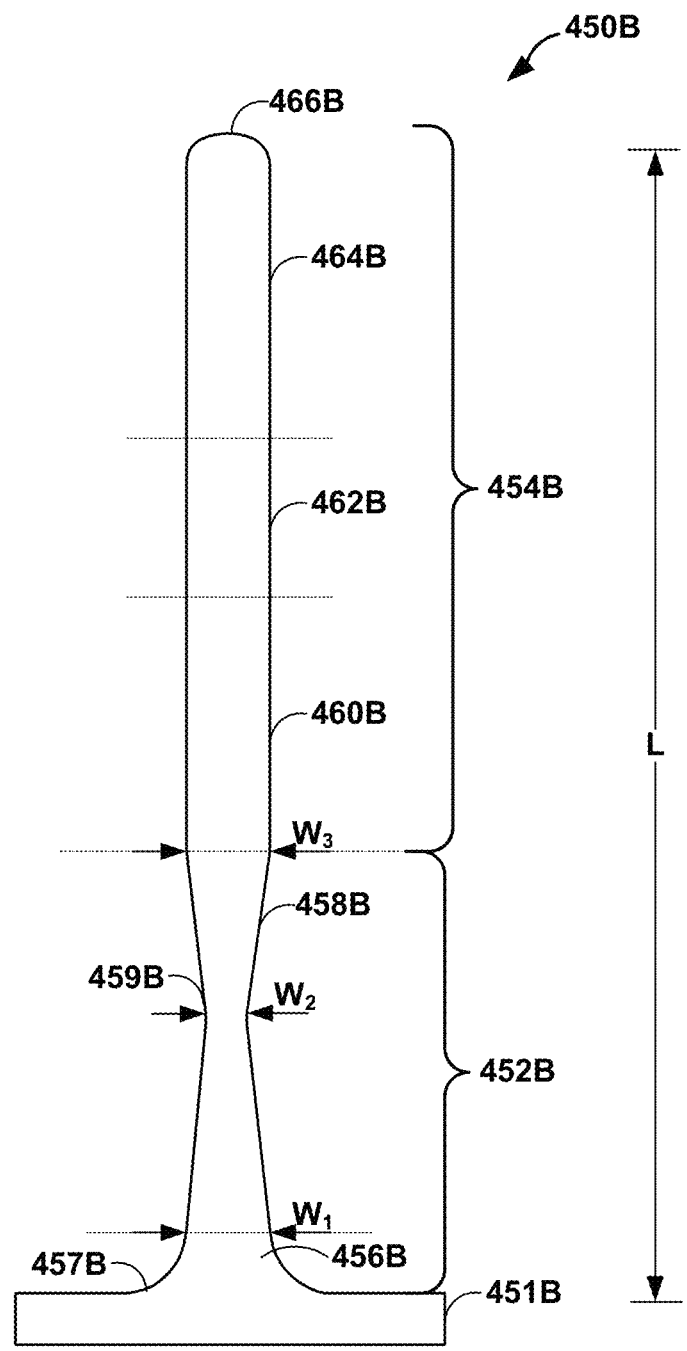

As illustrated in FIG. 4B, curved section 458B of tine 450B may include a tapered portion 459B. Tapered portion 459B includes a proximal width $W_1$, a medial (middle) width $W_2$, and a distal width $W_3$. In some examples, $W_1$ and $W_3$ may be the same or substantially similar, e.g., about 0.030 inch (0.762 mm), and $W_2$ may be about 0.025 inch (0.635 mm). Although illustrated as including three widths, in some examples, tapered portion 459B may include a plurality of tapers, each taper having a respective maximum width and respective minimum width. In some examples, tapered portion 459B may increase the flexibility of curved section 458B relative to an untampered curved section (e.g., curved section 458A illustrated in FIG. 4A). By increasing the flexibility of curved section 458B, tine 450B may have, after preforming curved section 458B as discussed above, an increased deflection stiffness compared to an untampered curved section. In some examples, distal portion 454B (e.g., proximal section 460B, curved section 462B, and tip 464B having free distal end 466B) may not include a tapered portion. By not including a tapered portion, tines 450B may have the same or substantially the same deployment stiffness compared to a tine having an untampered proximal portion (e.g., tine 450A). In this way, tines 450 may include one or more tapers to selectively control a deployment stiffness, a deflection stiffness, or both.

Figure 4C:
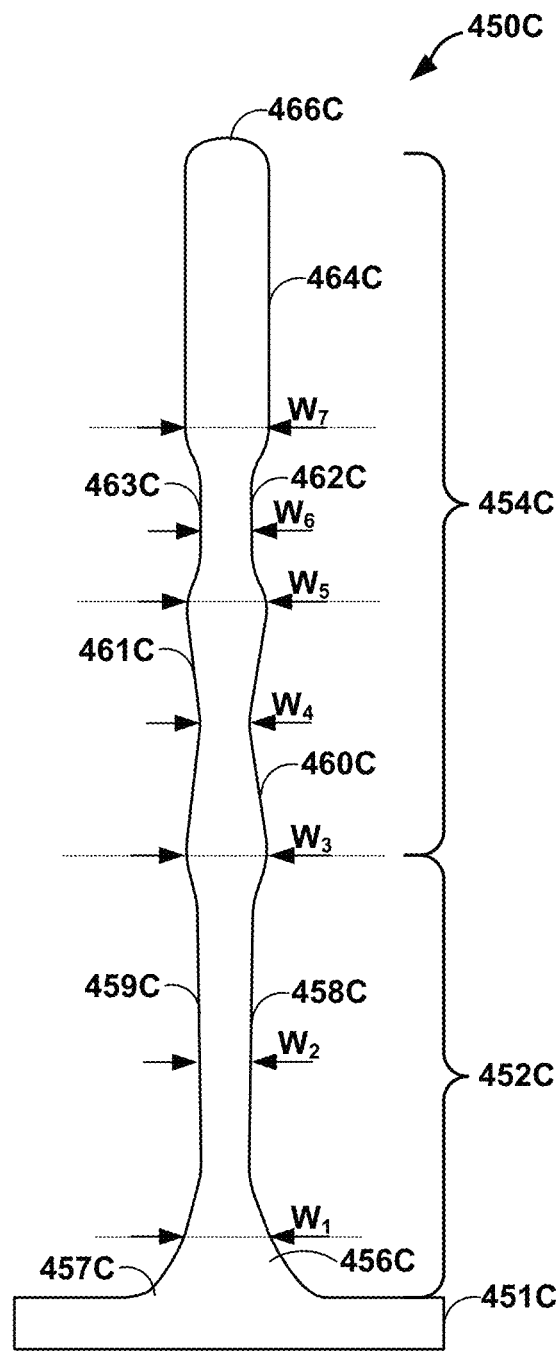

For example, as illustrated in FIG. 4C, tines 450C includes a plurality of tapers. Proximal section 456C may include fillet 457C extending from base 451C. Curved section 458C may extend from proximal section 456C and include a tapered portion 459C having a proximal width $W_1$, a medial width $W_2$, and a distal width $W_3$. Proximal section 460C of distal portion 454C may extend from curved section 458C and include a tapered portion 461C having a proximal width $W_3$, a medial width $W_4$, and a distal width $W_5$. Proximal section 460C of distal portion 454C may extend from curved section 458C and include a tapered portion 461C having a proximal width $W_3$, a medial width $W_4$, and a distal width $W_5$. Curved section 462C of distal portion 454C may extend from proximal section 462C and include a tapered portion 463C having a proximal width $W_5$, a medial width $W_6$, and a distal width $W_7$. As illustrated in FIG. 4C, each of tapers 459C, 461C, and 463C may include a unique shape. The unique shape of a respective tapered portion may be configured to have a target flexibility after preforming tine 450C, for example, such that tine 450C has a target deflection stiffness and deployment stiffness.

Figure 4D:
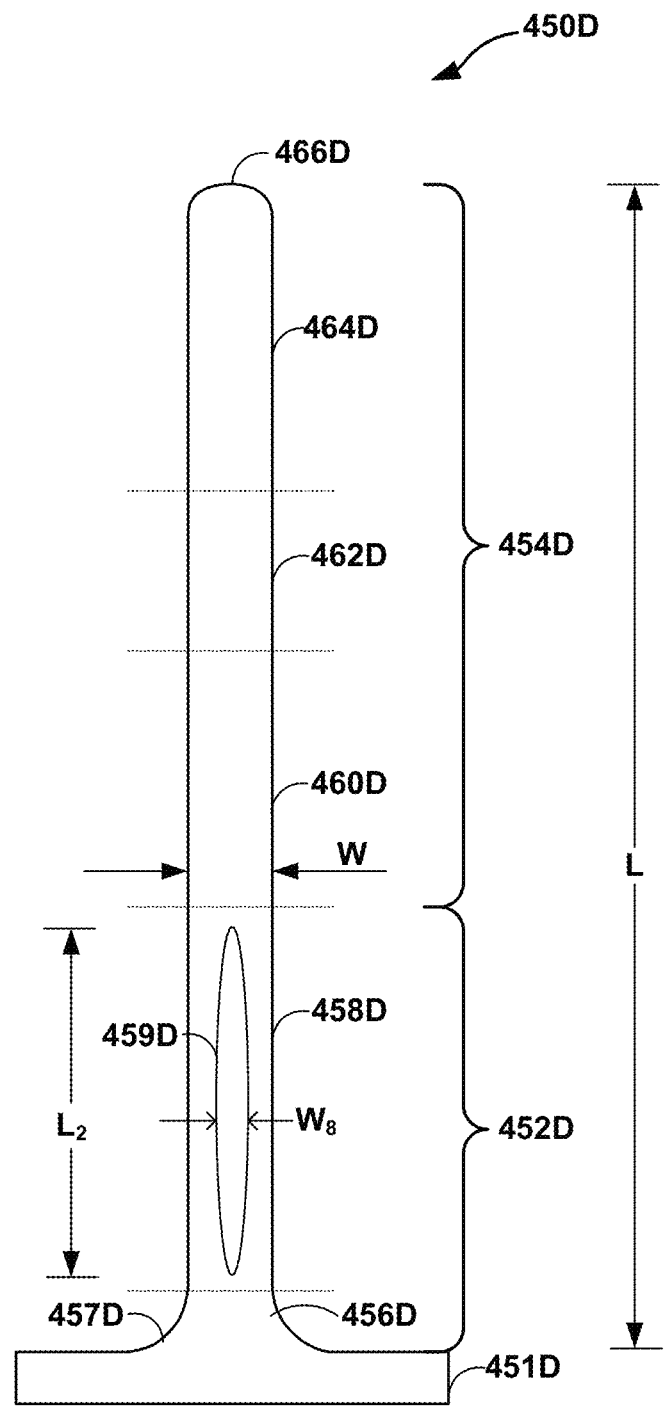

In some examples, rather than tapered portions, tines 450 may include cutouts, engravings, embossing, or other variations in the thickness of tines 450. For example, as illustrated in FIG. 4D, rather than a tapered portion, tine 450D includes cutout 458D having a width $W_8$ extending along a length $L_2$ of curved section 458C of proximal portion 452D. In some examples, cutout 458D may be configured to increase the flexibility of curved section 458D relative to an untampered curved section (e.g., curved section 458A illustrated in FIG. 4A). By increasing the flexibility of curved section 458D, tine 450D may have, after preforming curved section 458D as discussed above, an increased deflection stiffness compared to an untampered curved section.

Figure 4E:
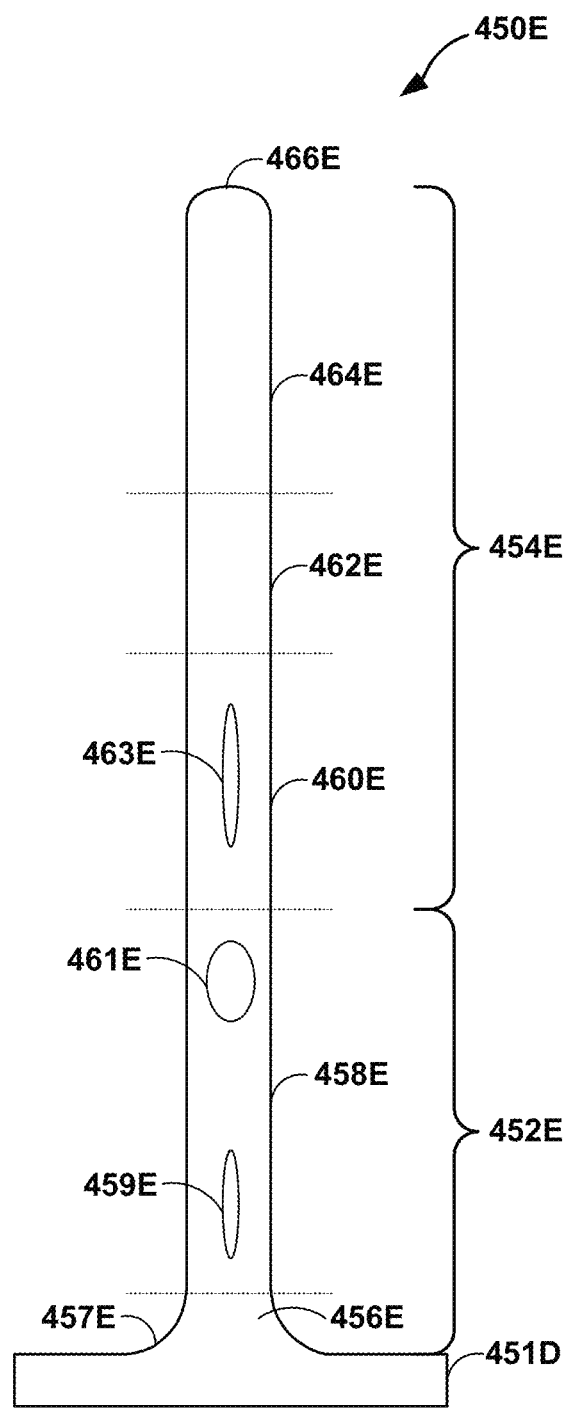

As illustrated in FIG. 4E, tine 450E include a plurality of cutouts 459E, 451E, and 453E. Similarly as discussed above in reference to FIG. 4C, each of cutouts 459E, 451E, and 453E may include a unique shape and position configured to result in a target flexibility of tine 450E (e.g., after preforming tine 450C), such that tine 450C has a target deflection stiffness and a target deployment stiffness.

Figure 5A:
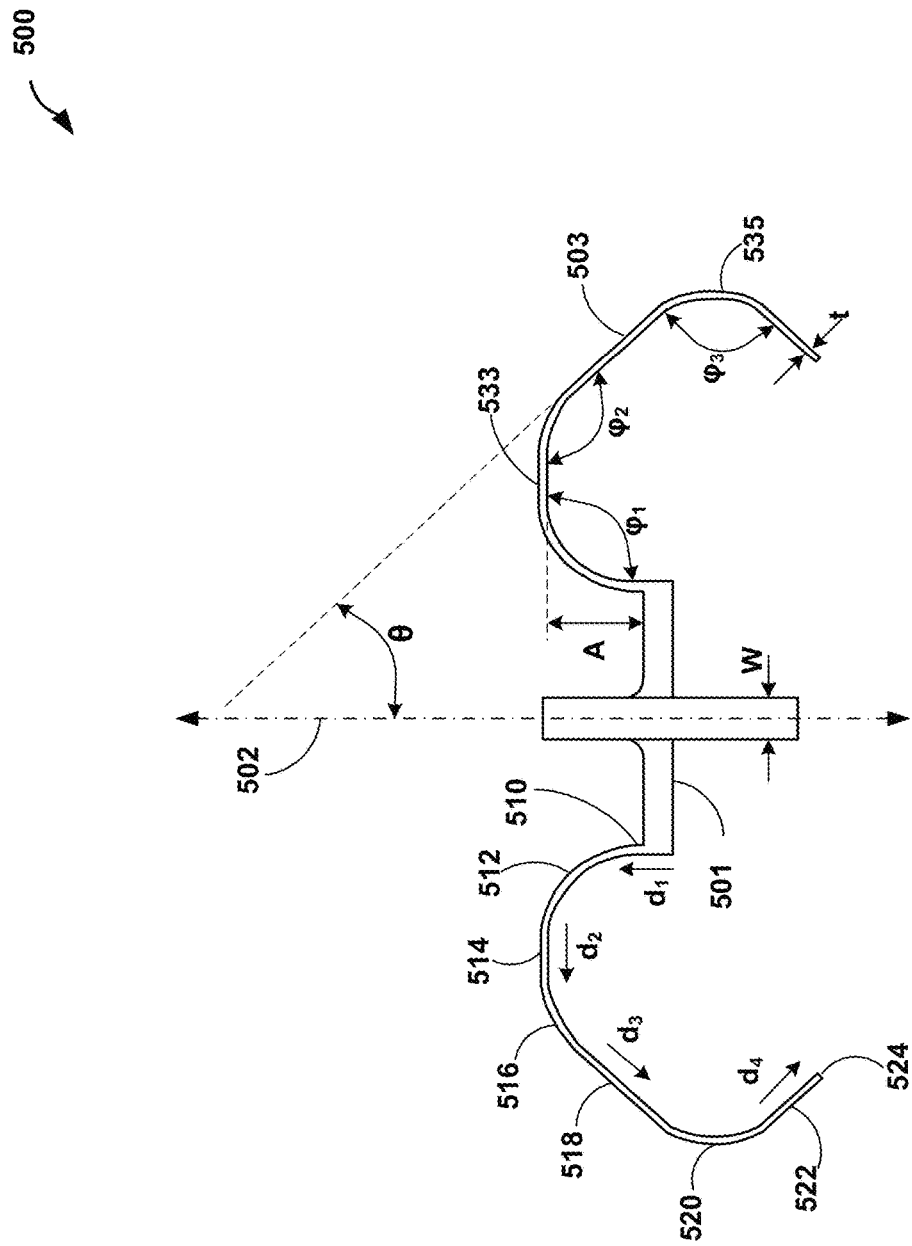
FIGS. 5A and 5B are conceptual diagrams illustrating an example three-knuckle fixation component.
Figure 5B:
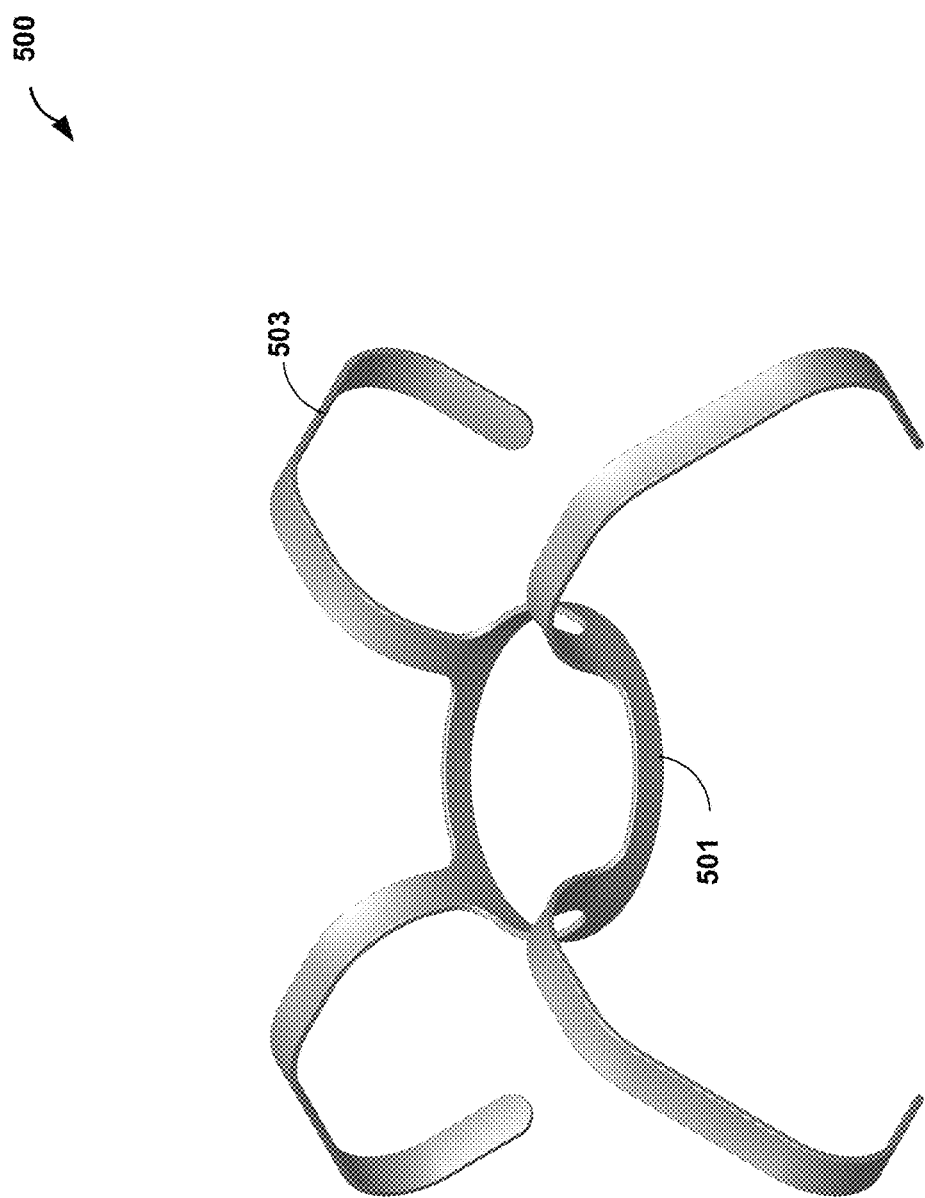

In some examples, the tines of a fixation component may include more than two curved sections to result in a target deflection stiffness and a target deployment stiffness. FIGS. 5A and 5B are conceptual diagrams illustrating an example three-knuckle fixation component 500. Three-knuckle fixation component 500 may be the same as or substantially similar to fixation component 30 and two-knuckle fixation component 300 discussed above in reference to FIGS. 2A-4E, except for the differences describe herein. For example, three-knuckle fixation component 500 includes a base 501 from which tines 503 extend and are spaced apart from one another around a perimeter of base 501. Base 501 may define a longitudinal axis 502 of three-knuckle fixation component 500, which may, in some examples, generally aligned along longitudinal axis 2 of IMD 20 (FIG. 2A).

As illustrated in FIG. 5A, each tine of tines 503 includes proximal portion 533 and distal portion 535 terminating in free distal end 552. Proximal section 510 of proximal portion 533 is fixedly attached to base 501. Proximal portion 533 may include a proximal section 510, a first curved section 512, a first straight section 514, and a second curved section 516, the first straight section 514 between the first and second curved sections 512 and 516. Each of proximal section 510, first curved section 512, first straight section 514, and second curved section 516 may be sized and shaped to enable tine 503 to have a target deflection stiffness and a target deployment stiffness.

Proximal section 510 extends in a first direction $d_1$. In some examples, first direction $d_1$ may be substantially parallel to longitudinal axis 502. In some examples, first direction $d_1$ may be an angle relative to longitudinal axis 502, such as for example, between about 0 degrees to about 5 degrees.

First curved section 512 may include a spring-biased pre-formed curvature. First curved section 512 extends from proximal section 510 laterally, outward from longitudinal axis 502 to first straight section 514. In some examples, first curved section 512 may include a single radius within a range from about 0.06 inch (1.524 mm) to about 0.08 inch (2.032 mm), such as 0.067 inch±0.010 inch (1.7018 mm±0.254 mm).

First straight section 514 may include a substantially straight segment extending in a second direction $d_2$ and along a relatively straight line to second curved section 516. In some examples, second direction $d_2$ may be perpendicular to longitudinal axis 502. In some examples, a length of first straight section 514 may be within a range from about 0.035 inch (0.889 mm) to about 0.045 inch (1.143 mm), such as about 0.04 inch (1.016 mm). First straight section 514 may be oriented by first curved section 512, when un-deformed, to extend away from longitudinal axis 502, such that proximal section 510 and first straight section 514 enclose an angle $\varphi_1$. In some examples, angle $\varphi_1$ may be within a range from about 75 degrees to about 105 degrees, such as about 90 degrees.

Second curved section 516 may include a spring-biased pre-formed curvature. Second curved section 516 extends from proximal section 510 laterally, outward from longitudinal axis 502 to second straight section 518 of distal portion 535. In some examples, second curved section 516 may include a single radius within a range from about 0.06 inch (1.524 mm) to about 0.08 inch (2.032 mm), such as 0.067 inch±0.010 inch (1.7018 mm±0.254 mm).

Distal portion 535 may include a second straight section 518, a third curved section 520, and a tip section 522. Second straight section 518 and/or third curved section 520 may be sized and shaped to enable tine 503 to have a target deflection stiffness, a target deployment stiffness, or both.

As discussed above, in some examples, the target deflection stiffness may be selected to enable tines 503 to deflect a predetermined amount to enable visualization of tines 503 under fluoroscopy. In some examples, the target deflection stiffness may be within a range from about 0.2 N to about 0.8 N, such as about 0.3 N to about 0.6 N. The deployment stiffness may include a measure of a force applied by tines 503 as tines 503 move from a deformed configuration to an undeformed configuration upon deployment of fixation component from distal opening of delivery tool such that free distal end 524 penetrates pectinate muscle PM. In some examples, the target deployment stiffness may be within a range from about 0.6 N to about 1.2 N.

Second straight section 518 may include a substantially straight segment extending in a third direction $d_3$ and along a relatively straight line (dashed line). In some examples, a length of second straight section 518 may be within a range from about 0.075 inch (1.905 mm) to 0.125 inch (3.175 mm) inch, such as 0.100 inch±0.005 inch (2.54 mm±0.127 mm). Second straight section 518 may be oriented by second curved section 516, when un-deformed, such that first straight section 514 and second straight section 518 enclose an angle $\varphi_2$. In some examples, angle $\varphi_2$ may be within a range from about 120 degrees to about 150 degrees, such as about 135 degrees.

Third curved section 520 may include a deformable pre-formed curvature. Third curved section 520 extends from second straight section 518 (in direction $d_3$) back toward longitudinal axis 502 to tip section 522. In some examples, third curved section 520, when un-deformed, is defined by a single radius within a range from about 0.045 inch (1.143 mm) to about 0.055 inch (1.397 mm), such as 0.05 inch±0.010 inch (1.27 mm±0.254 mm).

Tip section 522 may include a substantially straight segment extending in a fourth direction $d_4$ from third curved section 520 to free distal end 524. In some examples, a length of each tip section 522 may be within a range from about 0.045 inch (1.143 mm) to about 0.055 inch (1.397 mm), such as about 0.05 inch±0.010 inch (1.27 mm±0.254 mm). Tip section 522 is shown oriented by third curved section 520, when un-deformed, to extend toward longitudinal axis 502, such that tip section 522 and second straight section 518 are shown enclosing an angle $\varphi_3$. In some examples, angle $\varphi_3$ may be greater than or equal to about 90 degrees, such as in a range from about 90 degrees to about 120 degrees.

As discussed above in reference to FIGS. 2A-4E, the shaped configuration and width of each tine, e.g., tines 503, and, in some examples, the super-elastic stiffness properties of nickel-titanium alloy, enable each of tines 530 to produce a sufficient spring force and structural stiffness to engage tissue for the fixation of IMD 20 at an implant site when deployed by delivery tool 430, as described in greater detail below.

Figure 6:
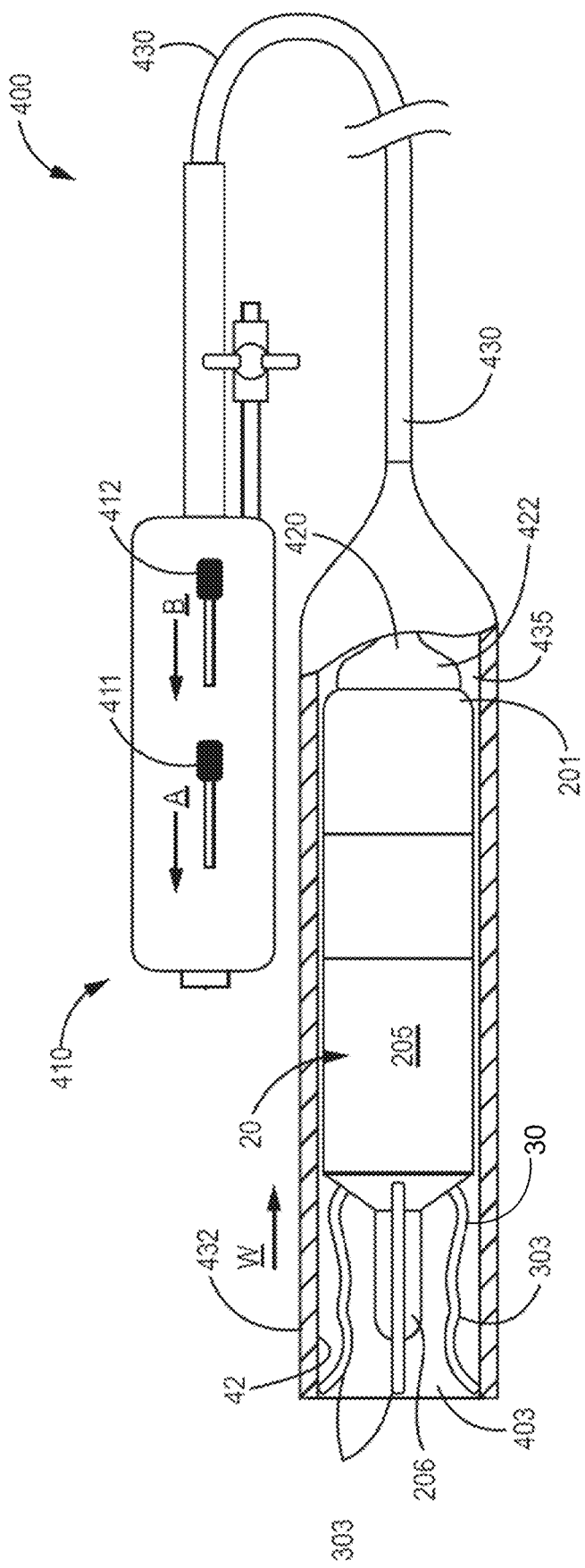
FIG. 6 is a conceptual diagram illustrating a plan view with a partial cut-away section of a medical device system including a delivery tool and an IMD.

FIG. 6 is a conceptual diagram illustrating a plan view with a partial cut-away section of a medical device system 400 including a delivery tool 430 and an IMD 20. For purposes of illustration, the distal end of delivery tool 430 is enlarged relative to handle 410. Additionally, although medical device system 400 is described in reference to fixation component 30 describe in reference to FIGS. 2A and 2B, in other examples, medical device system 400 may include other fixation components, such as two-knuckle fixation component 300 describe in reference to FIGS. 3A and 3B or three-knuckle fixation component 500 illustrated in reference to FIGS. 5A and 5B.

During use, IMD 20 is loaded into delivery tool 430 for deployment to a target implant site (e.g. target implant site 102). Delivery tool 430 includes a handle 410, an elongate outer member 430, and an elongate inner member 420 that extends within lumen 435 of outer member 430. Inner member 420 includes a distal end 422, which is configured to engage IMD 20 by abutting proximal end 201 of housing 205 (e.g., as shown in the cut-away section). An entirety of IMD 20 may be loaded within tubular sidewall 432 that defines a distal portion of outer member lumen 435, for example, having been loaded therein by pulling IMD 20, with housing proximal end 201 leading, in through lumen distal opening 403. In some examples, an inner surface 42 of tubular sidewall 432 engages tines 303 of fixation component 30 as IMD 20 is loaded into lumen 435 to deform tines 303 (per arrow L of FIG. 3A) and then to hold each tine 303 of the loaded IMD 20 in a deformed configuration, e.g., a spring-loaded configuration.

With further reference to FIG. 6, a proximal end of outer member 430 is coupled to a control member 412 of handle 410 such that an entirety of outer member 430 is movable with respect to inner member 420, via control member 412, for example, so that a clinician may retract outer member 430, per arrow W, relative to IMD 20 and inner member 420, to deploy IMD 20 out through distal opening 403, after positioning medical device system 400 in proximity to a target implant site. The clinician may position medical device system 400 by advancing delivery tool 403 through a venous system of the patient, for example, from a femoral venous access site and up through the inferior vena cava IVC (FIG. 1). Delivery tool 430 may include articulating features to facilitate the navigation of the distal portion of delivery tool 430. For example, inner member 420 of delivery tool 430 may include a pull wire assembly (not shown) integrated therein and being coupled to another control member 411 of handle 410 that, when moved per arrow A, causes inner member 420 and outer member 430 to bend along distal portions thereof. A length of outer member 430, between handle 410 and distal opening 403, when outer member 430 is in the position shown in FIG. 6, may be between about 103 cm and about 107 cm, for example, to reach into the right atrium RA from the femoral access site. Suitable construction detail for a delivery tool like delivery tool 430 is described in co-pending and commonly assigned U.S. Pat. No. 9,526,522 to Wood et al., which is incorporated herein by reference in its entirety.

According to some methods, once the clinician has advanced medical device system 400 target implant site 102 (FIG. 1), so that distal opening 403 abuts pectinate muscle PM therein (FIG. 2B) at the target implant site, the clinician can move control member 412, per arrow B, to retract outer member 430 relative to IMD 20 and thereby release the spring loading of three-knuckle fixation component 500 so that tines 303 engage with pectinate muscle PM to secure IMD 20 at the implant site, as illustrated in FIG. 2B. However, it should be noted that, according to alternative embodiments and methods, delivery tool 430 may be configured so that an clinician can advance inner member 420 relative to outer member 430 to push IMD 20 out through distal opening 403 for deployment.

Figure 7C:
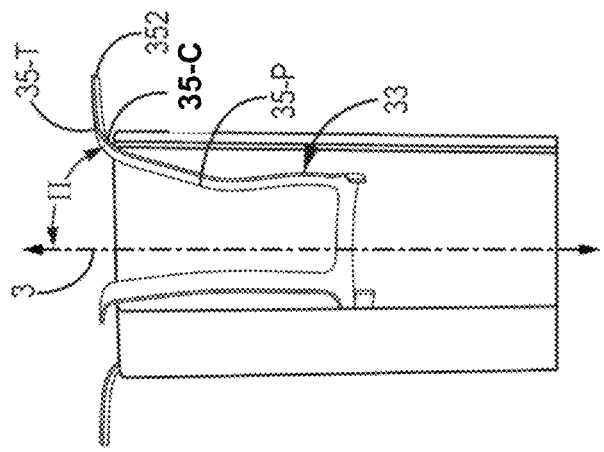
FIG. 7C is a conceptual diagram illustrating movement of the tines causing initial penetration of the tissue after the initial release of the fixation component.
Figure 7B:
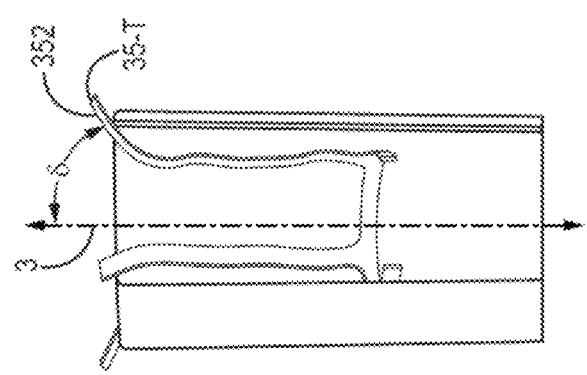
FIG. 7B is a conceptual diagram illustrating an initial release of the fixation component from the spring loaded configuration.
Figure 7A:
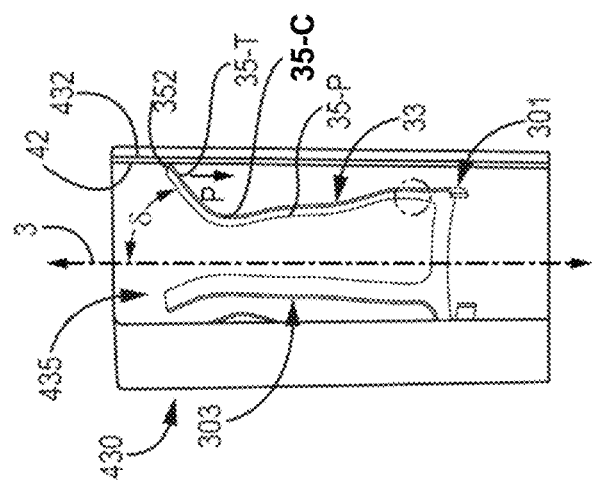
FIG. 7A is a conceptual diagram illustrating a spring loaded configuration of a fixation component within a lumen of a delivery tool.

FIGS. 7A-7F are conceptual diagrams illustrating a sequence of positions and/or configurations corresponding to the release of above-described fixation components. Although illustrated in reference to fixation component 30 describe in reference to FIGS. 2A and 2B, in other examples, delivery tool 430 may be configured to release other fixation components, such as two-knuckle fixation component 300 describe in reference to FIGS. 3A and 3B or three-knuckle fixation component 500 illustrated in reference to FIGS. 5A and 5B. FIG. 7A is a conceptual diagram illustrating a spring loaded configuration of a fixation component within a lumen of a delivery tool. FIG. 7A illustrates a maximum deformation of tines 303 when held in the spring loaded configuration by the engagement of free distal end 352 with inner surface 42 of outer member tubular sidewall 432. In some examples, proximal portion 33 becomes relatively straightened. In some examples, a location of the maximum principle strain along each tine 303 is in relatively close proximity to base 301 (designated by dashed-line circle). In some examples, the length of the tip section 35-T and the associated angle φ, as describe above in reference to FIG. 3A, help to keep the deformed tines 303 from touching one another within lumen 435 and to prevent free distal ends 352 from being pulled proximally, per arrow P, when outer member 430 is retracted to release the spring loading of tines 303.

FIG. 7A further illustrates tip section 35-T extending away from axis 3 at an acute angle δ, which is preferably in a range from about 45 degrees to about 75 degrees for an initial release of the spring loading of each tine 303. For example, FIG. 7B is a conceptual diagram illustrating an initial release of the fixation component from the spring loaded configuration. Upon retraction of outer member 430, tip sections 35-T extend past the distal opening of sidewall 432.

FIG. 7C is a conceptual diagram illustrating movement of the tines causing initial penetration of the tissue after the initial release of the fixation component. For example, once free distal end 352 is released from engagement with inner surface 42 for deployment into tissue at the implant site, the spring force of proximal portion 33 and the pre-formed curvature of curved section 35-C cause tip section 35-T to immediately rotate away from axis 3 to an angle π, which approaches 90 degrees, so that tip section 35-T is oriented approximately normal to axis 3 for initial penetration of pectinate muscle PM. Thus each tine free distal end 352 is deployed in a direction toward pectinate muscle PM that ultimately prevents tines 303 from perforating the underlying visceral pericardium VP (reference FIG. 2B).

FIGS. 7D-7F illustrate the subsequent movement of tines 303, being driven by the release of proximal portion 33 from the spring loaded configuration. FIG. 7D is a conceptual diagram illustrating further movement of the fixation component as the portions of the tines between the distal most and next proximal curves reaches the distal end of the delivery tool. As each tine of tines 303 moves from the position illustrated in FIG. 7C to the position illustrated in FIG. 7D, free distal end 352 may travel substantially transverse to longitudinal axis 3, thereby penetrating additional tissue. FIG. 7E is a conceptual diagram illustrating further movement fixation component as the proximal curve travels past the distal end of the delivery tool. FIG. 7F is a conceptual diagram illustrating final configuration of fixation component movement, subsequent to movement. As illustrated in FIGS. 7D-7F, the release of proximal portion 33 may cause free distal end 352 to curl back toward longitudinal axis 3, such that, after penetrating through pectinate muscle PM at a first location P1, tip section 35-T may penetrate back through pectinate muscle PM in an opposite direction at a second location P2, so that IMD 20 may be securely fixed at the implant site, as illustrated in FIG. 2B.

The configuration of distal portion 35, including, for example, the length of proximal section 35-P and tip section 35-T, and the pre-formed curvature of curved section 35-C, provide a structural stiffness and reach to each tine 303 that is sufficient for deformation and subsequent penetration of free distal end 352 through pectinate muscle PM, as shown in FIG. 2B, but is not sufficient for penetration through visceral pericardium VP. Even if the clinician ends up advancing medical device system 400 into target implant site 102 so that distal opening 403 of delivery tool 430 abuts visceral pericardium VP, between folds of pectinate muscle PM, free distal end 352, according to this configuration of tines 303, is not backed-up by sufficient stiffness to penetrate through visceral pericardium VP, so tip section 35-T of tine distal portion 35 is redirected, laterally, toward pectinate muscle PM.

Figure 8:
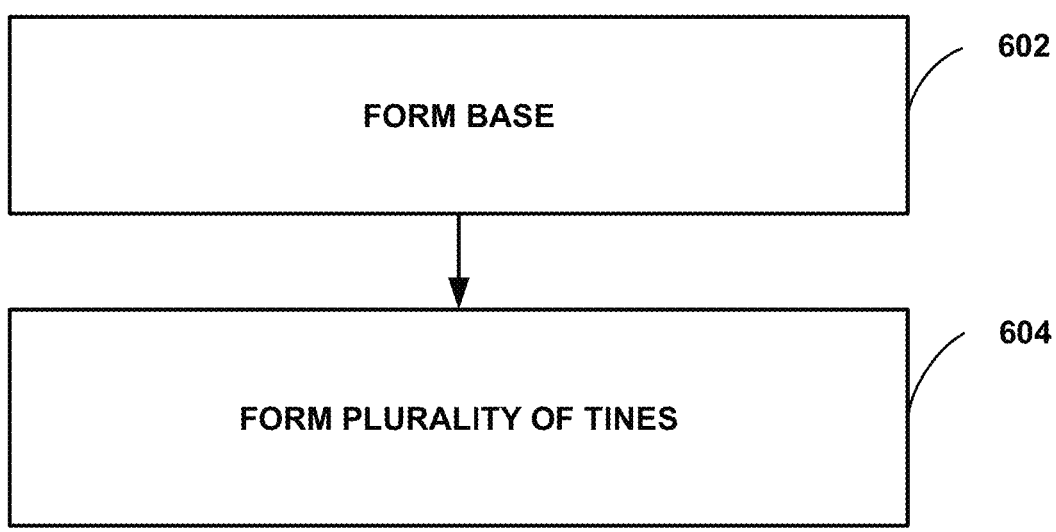
FIG. 8 is a flow diagram illustrating an example method of manufacturing a fixation component.

The fixation components described herein may be manufactured using any suitable technique. FIG. 8 is a flow diagram illustrating an example method of manufacturing a three-knuckle fixation component 500. Although the technique illustrated in FIG. 8 is described in reference to three-knuckle fixation component 500 illustrated in reference to FIGS. 5A and 5B, the technique may be used to manufacture other fixation component, such as fixation component 30 describe in reference to FIGS. 2A, 2B, 6, and 7A-7F, and two-knuckle fixation component 300 describe in reference to FIGS. 3A and 3B. Additionally, fixation component 30 and/or two-knuckle fixation component 300 may be manufactured using other techniques.

The technique illustrated in FIG. 8 includes forming base 501 defining longitudinal axis 502 of fixation component 500. In some examples, forming based 501 may include cutting a tube, such as a metal tube, a nickel titanium alloy tube, or a stainless steel tube, to define base 501. Forming base 501 may include pre-processing or post-processing steps, such as abrading, coating, heat treating, or polishing a substrate defining base 501.

The technique illustrated in FIG. 8 also includes forming tines 503 extending from base 501 and being spaced apart from one another. In some examples, base 501 and tines 503 may be integrally formed. For example, base 501 and tines 503 may be integrally formed from a tube, such as a metal tube, a nickel titanium alloy tube, or a stainless steel tube. In some examples, forming base 501 and tines 503 from a single tube may include removing material from the single tube to define base 501 and tines 503. In some examples, removing material from the single tube may include one or more of machining, chemical etching, laser etching, stamping, or water cutting. In some examples, forming tines 503 may include forming one or more tapers on one or more tines of the plurality of tines. For example, forming one or more tapers may include any other above techniques to remove material from the single tube. In some examples, one or more tapers may be formed while removing material form the single tube.

In some examples, forming tines 503 may include bending each tine of tines 503 to define first curved section 512, second curved section 516, and third curved section 520. In some examples, each curve and/or each tine of tines 503 may be bent individually or bend simultaneously, e.g., by use of a jig configured to bend one or more curves on one or more of tines 503. After bending (and holding in the bent configuration) tines 503, forming tines 503 also may include heat treating the bent tines 503 to cause the plurality of tines to hold the bent configuration. For example, heat treating the bent tines 503 may cause a microstructure of the material of tines 503 to assume a configuration such that a resting state of tines 503 (e.g., without application of an external force) is the bend configuration.

The following clauses illustrate example subject matter of the present disclosure.

Clause 1. A fixation component for an implantable medical device (IMD), comprising: a base defining a longitudinal axis of the fixation component, wherein the base is fixedly attached to the IMD having a proximal end and a distal end aligned along the longitudinal axis; and a plurality of tines extending from the base and being spaced apart from one another, each tine of the plurality of tines comprising: proximal portion comprising: a proximal section fixedly attached to the base and extending from the base in a first direction; a first curved section defining a first deformable pre-formed curvature and extending from the proximal section laterally, outward from the longitudinal axis; a first straight section extending from the first curved section laterally, outward from the longitudinal axis in a second direction; and a second curved section defining a second deformable pre-formed curvature and extending from the first straight section laterally, outward from the longitudinal axis; and a distal portion comprising: a second straight section extending from the second curved section in a third direction oriented generally opposite the first direction; a third curved section defining a third deformable pre-formed curvature and extending from the second straight section; and tip section extending from the third curved section toward the longitudinal axis and terminating in a free distal end.

Clause 2. The fixation component of clause 1, wherein the proximal portion is configured to have a deflection stiffness of less than about 0.6 Newtons (N).

Clause 3. The fixation component of clause 1 or 2, wherein the proximal portion is configured to have a deployment stiffness of more than about 0.6 N.

Clause 4. The fixation component of any one of clauses 1 through 3, wherein the first curved section, when in an undeformed configuration, is defined by a radius of the first deformable pre-formed curvature within a range from about 1.524 millimeters (mm) to about 2.032 mm.

Clause 5. The fixation component of any one of clauses 1 through 4, wherein the second curved section, when in an undeformed configuration, is defined by a radius of the second deformable pre-formed curvature within a range from 1.524 mm to about 2.032 mm.

Clause 6. The fixation component of any one of clauses 1 through 5, wherein the third curved section, when in an undeformed configuration, is defined by a radius of the third deformable pre-formed curvature within a range from about 1.143 mm to about 1.397 mm.

Clause 7. The fixation component of any one of clauses 1 through 6, wherein the first straight section has a length within a range from about 0.889 mm to about 1.143 mm.

Clause 8. The fixation component of any one of clauses 1 through 7, wherein the second straight section has a length within a range from about 1.905 mm to about 3.175 mm.

Clause 9. The fixation component of any one of clauses 1 through 8, wherein the first straight section and the second straight section enclose an angle within a range from about 120 degrees to about 150 degrees.

Clause 10. The fixation component of any one of clauses 1 through 9, wherein the tip section has a length within a range from about 1.143 mm to about 1.397 mm.

Clause 11. The fixation component of any one of clauses 1 through 10, wherein the third curve section, when undeformed, orients the tip section to enclose with the second straight section an angle within a range from about 90 degrees to about 120 degrees.

Clause 12. The fixation component of any one of clauses 1 through 11, wherein at least one of the first curve section or the second curve section comprises a tapered portion comprising a width of less than about 0.762 millimeters.

Clause 13. The fixation component of any one of clauses 1 through 12, wherein at least one of the first straight section, second straight section, or tip section comprises a tapered portion comprising a width of less than about 0.762 millimeters.

Clause 14. The fixation component of any one of clauses 1 through 13, wherein the tapered portion comprises a proximal portion having a width of about 0.762 mm, a medial portion having a width of about 0.635 mm, and a distal portion having width of about 0.762 mm.

Clause 15. The fixation component of any one of clauses 1 through 14, wherein the tapered portion comprises a change in a width of the tine of at least about 0.127 mm.

Clause 16. The fixation component of any one of clauses 1 through 15, wherein the tapered portion comprises a cutout, and wherein the width comprises a width of the tine less a widest portion of the cutout.

Clause 17. A fixation component for an implantable medical device (IMD), comprising: a base defining a longitudinal axis of the fixation component, wherein the base is fixedly attached to the IMD having a proximal end and a distal end aligned along the longitudinal axis; and a plurality of tines extending from the base and being spaced apart from one another, each tine of the plurality of tines comprising: a proximal portion comprising: a proximal section fixedly attached to the base and extending in a first direction generally parallel to the longitudinal axis; and a first curved section extending from the proximal section laterally, outward from the longitudinal axis, wherein the curved section is configured to provide a deflection stiffness of less than about 0.6 Newtons; a distal portion comprising: a second proximal section extending from the first curved section in a second direction oriented generally opposite the first direction; a second curved section having a deformable pre-formed curve and extending from the second proximal section; and tip section extending from the second curved section toward the longitudinal axis and terminating in a free distal end.

Clause 18. The fixation component of clause 17, wherein the first curved comprises a width of equal to or less than 0.635 millimeters.

Clause 19. The fixation component of clause 17 or 18, wherein at least a portion of a respective tine of the plurality of tines comprises a taper.

Clause 20. The fixation component of clause 19, wherein the portion of the respective tine comprises the second proximal section.

Clause 21. The fixation component of clause 19 or 20, wherein the taper comprises proximal portion having a width of about 0.762 mm, a medial portion having a width of about 0.635 mm, and a distal portion having width of about 0.762 mm.

Clause 22. The fixation component of any one of clauses 19 through 21, wherein the taper comprises a change in a width of the tine of at least about 0.127 mm.

Clause 23. The fixation component of any one of clauses 17 through 22, wherein the first curved section is defined by a single radius, the radius being between about 1.524 mm and about 2.032 mm.

Clause 24. The fixation component of any one of clauses 17 through 23, wherein the first curved section comprises a first deformable pre-formed curved section and a second deformable pre-formed curved section.

Clause 25. The fixation component of clause 24, wherein the first curved section further comprises a straight section extending between the first deformable pre-formed curved section and the second deformable pre-formed curved section.

Clause 26. The fixation component of clause 24 or 25, wherein the deflection stiffness of the first curved section is defined by a first radius of the first deformable pre-formed curvature when in an undeformed configuration, a second radius of the second deformable pre-formed curvature when in an undeformed configuration, and a length of the straight section extending therebetween.

Clause 27. An implantable medical device (IMD) comprising: a housing extending along a longitudinal axis from a proximal end to a distal end; an electrode mounted in proximity to the distal end of the housing; and a fixation component comprising a base in proximity to the distal end of the housing and a plurality of tines fixedly attached spaced from one another around a perimeter of the distal end of the housing, each tine of the plurality of tines comprising: a proximal portion comprising: a proximal section fixedly attached to the base and extending from the base in a first direction; a first curved section defining a first deformable pre-formed curvature and extending from the proximal section laterally, outward from the longitudinal axis; a first straight section extending from the first curved section laterally, outward from the longitudinal axis in a second direction; and a second curved section defining a second deformable pre-formed curvature and extending from the first straight section laterally, outward from the longitudinal axis; and a distal portion comprising: a second straight section extending from the second curved section in a third direction oriented generally opposite the first direction; a third curved section defining a third deformable pre-formed curvature and extending from the second straight section; and tip section extending from the third curved section toward the longitudinal axis and terminating in a free distal end.

Clause 28. The IMD of clause 27, wherein the proximal portion is configured to have a deflection stiffness of at least less than 0.6 N.

Clause 29. The IMD of clause 27 or 28, wherein the proximal portion is configured to have a deployment stiffness of at least more than 0.6 N.

Clause 30. A medical device system comprising: an implantable medical device (IMD) comprising: a housing extending along a longitudinal axis from a proximal end to a distal end; an electrode mounted in proximity to the distal end of the housing; and a fixation component comprising a base in proximity to the distal end of the housing and a plurality of tines fixedly attached spaced from one another around a perimeter of the distal end of the housing; and a delivery tool comprising a tubular sidewall that defines a lumen into which the IMD may be loaded, wherein the lumen having a distal opening through which the IMD may be deployed, wherein each tine of the plurality of tines comprises: proximal portion comprising: a proximal section fixedly attached to the base and extending from the base in a first direction; a first curved section defining a first deformable pre-formed curvature and extending from the proximal section laterally, outward from the longitudinal axis; a first straight section extending from the first curved section laterally, outward from the longitudinal axis in a second direction; and a second curved section defining a second deformable pre-formed curvature and extending from the first straight section laterally, outward from the longitudinal axis; and distal portion comprising: a second straight section extending from the second curved section in a third direction oriented generally opposite the first direction; a third curved section defining a third deformable pre-formed curvature and extending from the second straight section; and tip section extending from the third curved section toward the longitudinal axis and terminating in a free distal end.

Clause 31. The medical device system of clause 30, wherein the proximal portion is configured to have a deflection stiffness of at least less than 0.6 N.

Clause 32. The medical device system of clause 30 or 31, wherein the proximal portion is configured to have a deployment stiffness of at least more than 0.6 N.

Clause 33. The medical device system of any one of clauses 30 through 32, wherein, when the IMD is loaded within the lumen of the delivery tool, the free distal end of each tine of the fixation component engages an inner surface of the tubular sidewall in proximity to the distal opening of the delivery tool to hold at least one of the first curved section, the second curved section, or the third curved section of each tine of the plurality of tines in a spring loaded configuration in which: each tip section extends away from the longitudinal axis at an acute angle in a range from about 45 degrees to about 75 degrees for deployment of the corresponding free distal end out from the distal opening;

and upon deployment, each tip section rotates away from the longitudinal axis to approach an angle of about 90 degrees relative to the longitudinal axis in response to an initial release of the spring loaded configuration of at least one of the first curved section, the second curved section, or the third curved section of each tine of the plurality of tines.

Clause 34. A method of forming a fixation component for an IMD comprising: forming a base defining a longitudinal axis of the fixation component; and forming a plurality of tines extending from the base and being spaced apart from one another, each tine of the plurality of tines comprising: a proximal portion comprising: a proximal section fixedly attached to the base and extending from the base in a first direction; a first curved section defining a first deformable pre-formed curvature and extending from the proximal section laterally, outward from the longitudinal axis; a first straight section extending from the first curved section laterally, outward from the longitudinal axis in a second direction; and a second curved section defining a second deformable pre-formed curvature and extending from the first straight section laterally, outward from the longitudinal axis; and a distal portion comprising: a second straight section extending from the second curved section in a third direction oriented generally opposite the first direction; a third curved section defining a third deformable pre-formed curvature and extending from the second straight section; and tip section extending from the third curved section toward the longitudinal axis and terminating in a free distal end.

Clause 35. The method of clause 34, wherein the base and the plurality of tines are integrally formed from a tube by removing material from the tube to define the base and the plurality of tines.

Clause 36. The method of clause 34 or 35, wherein forming the plurality of tines comprises: bending each tine of the plurality of tines to define the first curved section, the second curved section, and the third curved section; and heat treating the bent plurality of tines to cause the plurality of tines to hold the bent configuration.

Clause 37. The method of any one of clauses 34 through 36, wherein the method comprises forming one or more tapers on one or more tines of the plurality of tines.

Various examples of the disclosure have been described. Any combination of the described systems, operations, or functions is contemplated. These and other examples are within the scope of the following claims.

What is claimed is:

1. A fixation component for an implantable medical device (IMD), comprising:
 a base defining a longitudinal axis of the fixation component, wherein the base is fixedly attached to the IMD having a proximal end and a distal end aligned along the longitudinal axis; and
 a plurality of tines extending from the base and being spaced apart from one another, each tine of the plurality of tines comprising, when in an undeformed configuration:
 a proximal portion comprising:
  a proximal section fixedly attached to the base and extending from the base in a first direction;
  a first curved section defining a first deformable pre-formed curvature and extending from the proximal section laterally, outward from the longitudinal axis;
  a first straight section extending from the first curved section laterally, outward from the longitudinal axis in a second direction; and
  a second curved section defining a second deformable pre-formed curvature and extending from the first straight section laterally, outward from the longitudinal axis; and
 a distal portion comprising:
  a second straight section extending from the second curved section in a third direction oriented generally opposite the first direction;
  a third curved section defining a third deformable pre-formed curvature and extending from the second straight section; and
  a tip section extending from the third curved section toward the longitudinal axis and terminating in a free distal end.

2. The fixation component of claim 1, wherein the proximal portion is configured to have a deflection stiffness of less than about 0.6 Newtons (N).

3. The fixation component of claim 1, wherein the proximal portion is configured to have a deployment stiffness of more than about 0.6 N.

4. The fixation component of claim 1, wherein the first curved section, when in an undeformed configuration, is defined by a radius of the first deformable pre-formed curvature within a range from about 1.524 millimeters (mm) to about 2.032 mm.

5. The fixation component of claim 1, wherein the second curved section, when in an undeformed configuration, is defined by a radius of the second deformable pre-formed curvature within a range from 1.524 mm to about 2.032 mm.

6. The fixation component of claim 1, wherein the third curved section, when in an undeformed configuration, is defined by a radius of the third deformable pre-formed curvature within a range from about 1.143 mm to about 1.397 mm.

7. The fixation component of claim 1, wherein the first straight section has a length within a range from about 0.889 mm to about 1.143 mm.

8. The fixation component of claim 1, wherein the second straight section has a length within a range from about 1.905 mm to about 3.175 mm.

9. The fixation component of claim 1, wherein the first straight section and the second straight section enclose an angle within a range from about 120 degrees to about 150 degrees.

10. The fixation component of claim 1, wherein the tip section has a length within a range from about 1.143 mm to about 1.397 mm.

11. The fixation component of claim 1, wherein the third curve section, when un-deformed, orients the tip section to enclose with the second straight section an angle within a range from about 90 degrees to about 120 degrees.

12. The fixation component of claim 1, wherein at least one of the first curve section or the second curve section comprises a tapered portion comprising a width of less than about 0.762 millimeters.

13. The fixation component of claim 1, wherein at least one of the first straight section, second straight section, or tip section comprises a tapered portion comprising a width of less than about 0.762 millimeters.

14. The fixation component of claim 1, wherein a tapered portion comprises a proximal portion having a width of about 0.762 mm, a medial portion having a width of about 0.635 mm, and a distal portion having width of about 0.762 mm.

15. The fixation component of claim 1, wherein a tapered portion comprises a change in a width of the tine of at least about 0.127 mm.

16. The fixation component of claim 1, wherein a tapered portion comprises a cutout, and wherein the width comprises a width of the tine less a widest portion of the cutout.

17. An implantable medical device (IMD) comprising:
a housing extending along a longitudinal axis from a proximal end to a distal end;
an electrode mounted in proximity to the distal end of the housing; and
a fixation component comprising a base in proximity to the distal end of the housing and a plurality of tines fixedly attached spaced from one another around a perimeter of the distal end of the housing, each tine of the plurality of tines comprising, when in an undeformed configuration:
a proximal portion comprising:
a proximal section fixedly attached to the base and extending from the base in a first direction;
a first curved section defining a first deformable pre-formed curvature and extending from the proximal section laterally, outward from the longitudinal axis;
a first straight section extending from the first curved section laterally, outward from the longitudinal axis in a second direction; and
a second curved section defining a second deformable pre-formed curvature and extending from the first straight section laterally, outward from the longitudinal axis; and
a distal portion comprising:
a second straight section extending from the second curved section in a third direction oriented generally opposite the first direction;
a third curved section defining a third deformable pre-formed curvature and extending from the second straight section; and
a tip section extending from the third curved section toward the longitudinal axis and terminating in a free distal end.

18. The IMD of claim 17, wherein the proximal portion is configured to have a deflection stiffness of at least less than 0.6 N.

19. The IMD of claim 17, wherein the proximal portion is configured to have a deployment stiffness of at least more than 0.6 N.

20. A medical device system comprising:
an implantable medical device (IMD) comprising:
a housing extending along a longitudinal axis from a proximal end to a distal end;
an electrode mounted in proximity to the distal end of the housing; and
a fixation component comprising a base in proximity to the distal end of the housing and a plurality of tines fixedly attached spaced from one another around a perimeter of the distal end of the housing; and
a delivery tool comprising a tubular sidewall that defines a lumen into which the IMD may be loaded, wherein the lumen having a distal opening through which the IMD may be deployed,
wherein each tine of the plurality of tines comprises, when in an undeformed configuration:
a proximal portion comprising:
a proximal section fixedly attached to the base and extending from the base in a first direction;
a first curved section defining a first deformable pre-formed curvature and extending from the proximal section laterally, outward from the longitudinal axis;
a first straight section extending from the first curved section laterally, outward from the longitudinal axis in a second direction; and
a second curved section defining a second deformable pre-formed curvature and extending from the first straight section laterally, outward from the longitudinal axis; and
a distal portion comprising:
a second straight section extending from the second curved section in a third direction oriented generally opposite the first direction;
a third curved section defining a third deformable pre-formed curvature and extending from the second straight section; and
a tip section extending from the third curved section toward the longitudinal axis and terminating in a free distal end.

21. The medical device system of claim 20, wherein the proximal portion is configured to have a deflection stiffness of at least less than 0.6 N.

22. The medical device system of claim 20, wherein the proximal portion is configured to have a deployment stiffness of at least more than 0.6 N.

23. The medical device system of claim 20, wherein, when the IMD is loaded within the lumen of the delivery tool, the free distal end of each tine of the fixation component engages an inner surface of the tubular sidewall in proximity to the distal opening of the delivery tool to hold at least one of the first curved section, the second curved section, or the third curved section of each tine of the plurality of tines in a spring loaded configuration in which:
each tip section extends away from the longitudinal axis at an acute angle in a range from about 45 degrees to about 75 degrees for deployment of the corresponding free distal end out from the distal opening; and
upon deployment, each tip section rotates away from the longitudinal axis to approach an angle of about 90 degrees relative to the longitudinal axis in response to an initial release of the spring loaded configuration of at least one of the first curved section, the second curved section, or the third curved section of each tine of the plurality of tines.

24. A method of forming a fixation component for an IMD comprising:
forming a base defining a longitudinal axis of the fixation component; and
forming a plurality of tines extending from the base and being spaced apart from one another, each tine of the plurality of tines comprising, when in an undeformed configuration:
a proximal portion comprising:
a proximal section fixedly attached to the base and extending from the base in a first direction;
a first curved section defining a first deformable pre-formed curvature and extending from the proximal section laterally, outward from the longitudinal axis;
a first straight section extending from the first curved section laterally, outward from the longitudinal axis in a second direction; and
a second curved section defining a second deformable pre-formed curvature and extending from the first straight section laterally, outward from the longitudinal axis; and
a distal portion comprising:
a second straight section extending from the second curved section in a third direction oriented generally opposite the first direction;

a third curved section defining a third deformable pre-formed curvature and extending from the second straight section; and a tip section extending from the third curved section toward the longitudinal axis and terminating in a free distal end.

25. The method of claim 24, wherein the base and the plurality of tines are integrally formed from a tube by removing material from the tube to define the base and the plurality of tines.

26. The method of claim 24, wherein forming the plurality of tines comprises:

bending each tine of the plurality of tines to define the first curved section, the second curved section, and the third curved section; and heat treating the bent plurality of tines to cause the plurality of tines to hold the bent configuration.

27. The method of claim 24, wherein the method comprises forming one or more tapers on one or more tines of the plurality of tines.

28. The fixation component of claim 1, wherein at least a portion of a respective tine of the plurality of tines comprises a cutout.

29. The fixation component of claim 28, wherein the cutout is configured to increase the flexibility of the portion of the respective tine of the plurality of tines comprising the cutout.

30. The fixation component of claim 28, wherein the portion of the respective tine comprises the first curved section.

31. The fixation component of claim 28, wherein the first curved section is configured to provide a deflection stiffness of less than about 0.6 Newtons due, at least in part, to the cutout.

* * * * *